(12) United States Patent
Schmidt

(10) Patent No.: US 6,219,622 B1
(45) Date of Patent: Apr. 17, 2001

(54) COMPUTATIONAL METHOD FOR DESIGNING CHEMICAL STRUCTURES HAVING COMMON FUNCTIONAL CHARACTERISTICS

(75) Inventor: Jonathan M. Schmidt, Elora (CA)

(73) Assignee: University of Guelph, Guelph (CA)

( * ) Notice: Subject to any disclaimer, the term of this patent is extended or adjusted under 35 U.S.C. 154(b) by 0 days.

This patent is subject to a terminal disclaimer.

(21) Appl. No.: 08/991,430

(22) Filed: Dec. 16, 1997

Related U.S. Application Data

(63) Continuation-in-part of application No. 08/485,272, filed on Jun. 7, 1995, now Pat. No. 5,699,268.

(30) Foreign Application Priority Data

Mar. 24, 1995 (GB) .................................... 9506048
May 9, 1995 (GB) .................................... 9509320

(51) Int. Cl.[7] .......................... G01N 31/00; G01N 33/53; L12Q 1/68; C07H 21/04
(52) U.S. Cl. ................................. 702/27; 435/6; 435/7.1; 536/22.1; 536/23.1; 530/300; 530/388.9
(58) Field of Search .................................. 364/496, 497, 364/498, 499, 512, 527, 550; 435/6, 7.1; 536/22.1, 23.1; 530/300, 388.9; 702/27

(56) References Cited

U.S. PATENT DOCUMENTS 5,434,796 * 7/1995 Weininger ........................... 364/496

OTHER PUBLICATIONS

Blanco, "Molecular Silverware: I. General Solutions to Excluded Volume Constrained Problems" J. of Computational Chem. 12(2):237–247, 1991.

Carneiro et al., "Rethinking 'Shape Space': Evidence from Simulated Docking Suggests that Seric Shape Complementarity . . . " J. Theor. Biol. 169:391–402, 1994.

Clark et al., "Pro–Ligand: An Approach to De Novo Molecular Design. I. Application to the Design of Organic Molecules" J. of Computer–Aided Molecular Design, pp. 13–32, 1995.

Dean, "Molecular Recognition: The measurement and Search for Molecular Similarity in Ligand–Receptor Interaction" Concepts and Applications of Molecular Similarity, pp. 211–238.

Walters et al., "Genetically Evolved Receptor Models: A Computational Approach to Construction of Receptor Models" Amer. Chemical Society, 1994.

* cited by examiner

Primary Examiner—Kenneth R. Horlick
Assistant Examiner—Jeffrey Siew
(74) Attorney, Agent, or Firm—Fish & Richardson P.C.

(57) ABSTRACT

The present invention related to computational methods for designing chemical structures sharing common, useful, functional properties based on specific combinations of steric configuration and binding affinity. More particularly the present invention provides a method for producing computer-simulated receptors which functionally mimic biological receptors. The simulated receptors are designed to exhibit optimized selective affinity for known target molecules. Chemical structures are then generated and evolved to exhibit selective affinity for the simulated receptors.

9 Claims, 4 Drawing Sheets

COMPUTATIONAL METHOD FOR DESIGNING CHEMICAL STRUCTURES HAVING COMMON FUNCTIONAL CHARACTERISTICS

CROSS REFERENCE TO RELATED U.S. PATENT APPLICATION

This patent application is a continuation-in-part application of U.S. patent application Ser. No. 08/485,272, filed on Jun. 7, 1995, entitled COMPUTATIONAL METHOD FOR DESIGNING CHEMICAL STRUCTURES HAVING COMMON FUNCTIONAL CHARACTERISTICS, now U.S. Pat. No. 5,699,268, which claims the benefit of foreign priority under 35 U.S.C. §119 of GB 4506048 filed Mar. 24, 1995, and GB 95093209, filed May 9, 1995. The disclosure of the prior applications are considered part of (and are incorporated by reference in) the disclosure of this application.

FIELD OF THE INVENTION

The present invention relates to a computer-based methods for designing chemical structures sharing common useful, functional properties based on specific combinations of steric configuration and binding affinity. More particularly the present invention provides a method for producing computer-simulated receptors which functionally mimic biological receptors. The simulated receptors are designed to exhibit optimized selective affinity for known target molecules. Chemical structures are then generated and evolved to exhibit selective affinity for the simulated receptors.

BACKGROUND OF THE INVENTION

Biological receptors are linear polymers of either amino acids or nucleotides that are folded to create three-dimensional envelopes for substrate binding. The specific three-dimensional arrangements of these linear arrays, and the placement of charged sites on the envelope surface are the products of evolutionary selection on the basis of functional efficacy. Biological receptors including antibodies, enzymes, ribozymes and transport proteins to mention just a few bind selectively to specific sets of compounds and the stereospecific and selective interactions between the relevant molecular species forms the basis of antibody-antigen interactions, biological toxicity and drug design. Although non-specific binding occurs, the functionality of receptors is generally dependent on their capacity to bind with high affinity to a limited set of substrates. For example, the immune system of vertebrates relies on the ability of antibodies to bind to a specific set of antigens.

The selectivity of biological receptors depends upon differences in the strength of attractive and repulsive forces generated between the receptor and the substrate. The magnitude of these forces varies in part with the magnitude and proximity of charged sites on the receptor and substrate surfaces. Charge sites can be formed by ionization of the substrate due to the addition or removal of electrons. Charge sites also arise in neutral, polar molecules due to asymmetrical sharing of electrons in covalent bonds. Electronegative atoms acquire partial negative charges by displacement of electrons away from less electronegative atoms. The resulting charge asymmetry generates a local or atomic dipole moment. Charge sites can also be induced when an uncharged molecule is brought into close proximity with a charged site on the receptor surface. Under these conditions a partial displacement of the electron orbitals in the portion of the substrate close to the charge site on the receptor may induce a net local charge. The strength of these induced charges varies with the susceptibility of the electrons in the affected portion of the substrate to displacement (polarizability), as well as the strength and proximity of the charged site on the receptor.

Because substrates differ in the number and magnitude of the charged sites present or induced on their surfaces, as well as the spatial arrangement of these sites, binding affinity can vary with substrate structure. Substrates with similar binding affinities for the same receptor have a high likelihood of sharing a common spatial arrangement of at least some of their induced and fixed charged sites. If the function of the receptor is correlated with binding affinity, then substrates with similar binding affinities will also be functionally similar in their effects. It is in this sense the receptor can be said to recognize or quantify similarities between the substrates.

Recent advances in molecular theory have made numerous contributions to the design of drugs, pesticides and polymers. Molecular theory provides tools based on quantum chemical techniques and a variety of methods that make use of molecular dynamics and Monte Carlo simulations based on empirical potential energy functions. These methods are applied to the determination of the geometric and electronic structural properties of bioactive molecules and polymers. Two principal concerns in the development of these methods are the electronic characteristics (e.g. charge-distribution, dipole and quadrapole moments and molecular electrostatic potential) and the nature of the active or functional conformation of a molecule.

A significant computational tool in this field is high-resolution force-field simulation based on data from simple experimental systems or ab initio quantum mechanical calculations. Similar approaches can be used to generate models of the distribution of charges over a molecular surface. Such quantum chemical approaches can be applied to a wide variety of small molecules. However, these methods are limited by the significant number of torsional degrees of freedom and corresponding conformational complexity of large molecules.

An important focus of these studies is the description of stereospecific and selective interactions between two molecular species, including antigens and antibodies or pharmacophores and target proteins. Such analyses at the level of individual molecules can be critical steps in the design of novel compounds with specific properties or functions. Descriptions of molecular interactions can be made by empirical description of the participating molecular species, for example by NMR or X-ray crystallography. Alternatively, one or both of the participating molecules may be modeled by a chemical or computational surrogate or model. Antibodies generated for various pharmacophores and toxophores are used as structural models of the active sites of their targets. Phage display of antibody proteins can also be used to develop structural models of receptors and the identification of selective ribozymes generated by combinatorial techniques represents a similar approach to the indirect description of biological target sites.

The structures of many protein receptor molecules have been determined by x-ray crystallography and NMR. This data is the basis for structure-based design of novel pharmaceutical agents (Kuntz, I. D. et al. (1982) J. Mol. Biol. 161: 269). When the proposed target protein cannot be identified or characterized directly, alternative computational techniques, including homology modelling (Blundell, T. L. et al. (1987) Nature, 326: 347), pharmacophore mapping (Martin, Y. C. et al. (1993) J. Comput.-Aided Design 7: 83) and comparative molecular field analysis (ComFA) (Cramer, R. D. et al. (1988) J. Am. Chem. Soc. 110: 5959) have been used to design pharmacophores that can interact with the receptor.

Traditional methods used in molecular recognition to identify or discover novel chemical compounds or substrates for selective binding affinity to receptors are based on finding molecular common subgraphs of active substrates and using these to predict new, similar compounds. A drawback to this technique is that it presupposes substrates exhibiting a similar efficacy for binding are structurally similar. In many cases however structurally dissimilar substrates can exhibit similar binding affinities for the same receptor. More current techniques based on quantitative structure-activity relationships (QSAR) are suited only to developing novel compounds within the same structural class and is largely inadequate at developing new molecular structures exhibiting the desired selective affinity, see for example Dean, Philip M., "Molecular Recognition: The Measurement and Search For Molecular Similarity in Ligand-Receptor Interaction", in Concepts and Applications of Molecular Similarity, Ed. Mark A. Johnson and Gerald M. Maggiora, pp. 211–238 (1990).

Recent efforts have been directed at the construction of atomic models of either pseudoreceptors, in which atoms and functional groups are connected, or minireceptors, comprised of unconnected sets of atoms or functional groups (Snyder, J. P. (1993) In 3D QSAR in Drug Design: Theory, Methods and Applications; Kubinyi, H. Ed.; Escom, Leiden. P. 336). Related methods involve surrounding known target ligands with a number of model atoms and calculation of the intermolecular forces generated between the ligand and the receptor model. Such models have a high correlation between calculated binding energy and biological activity (Walters, D. E. and Hinds, R. M. (1994) J. Medic. Chem. 37: 2527) but have not been developed to the point where novel chemical structures exhibiting selective affinity for the receptor models can be produced.

Therefore, it would be very advantageous to provide a method for identifying non-trivial similarities between different chemical structures which are both sufficient and necessary to account for their shared properties which can then be used as the basis for the design of new chemical structures with useful functional properties based on specific combinations of steric configuration and binding affinity.

SUMMARY OF THE INVENTION

The present invention provides a method for identifying non-trivial similarities between different chemical structures which are both necessary and sufficient to account for their shared functional properties. The process also provides a method of generating novel chemical structures that display similar functional properties. The basic concept underlying the present invention is the use of a two-step computational process to design or discover chemical structures with useful functional properties based on specific combinations of steric configuration and binding affinity. In the first step of this process an algorithmic emulation of antibody formation is used to create a population of computer-generated simulated receptors that mimic biological receptors with optimized binding affinity for selected target substrates. In the second stage of the process the simulated or virtual receptors are used to evaluate the binding affinity of existing compounds or to design novel substrates with optimal binding.

The method described herein provides simulated receptors which mimic selected features of biological receptors, including the evolutionary processes that optimize their binding selectivity. The mimics or simulated receptors generated by the method can be used to recognize specific similarities between molecules. Like antibodies and other biological receptors, the simulated receptors generated by this invention are feature extraction mechanisms: they can be used to identify or recognize common or similar structural features of target substrates. Binding affinity between the receptors and the target substrates is used as a metric for feature recognition. Target substrates can be quantitatively categorized on the basis of binding affinity with a specific simulated receptor. Compounds sharing specific structural features will also share similar binding affinities for the same virtual receptor.

Binding affinity between biological receptors and substrates is determined by the steric goodness of fit between the adjacent receptor and substrate surfaces, the exclusion of water between non-polar regions of the two surfaces and the strength of electrostatic forces generated between neighboring charged sites. In some cases the formation of covalent bonds between the substrate and the receptor may also contribute to binding affinity. The simulated receptors generated by this process mimic the binding mechanisms of their biological counterparts. Average proximity of the receptor and target surfaces and the strength of electrostatic attractions developed between charged sites on both surfaces are used to calculate a measurement of binding affinity. The resulting values for binding affinity are used to evaluate substrate molecular similarities.

Binding affinity can be globally determined, that is, dependent upon interactions between the entire substrate surface and a closed receptor or receptor envelope that completely surrounds the substrate. In this case analysis of global similarities between substrates is appropriate as a basis for developing useful quantitative structure-activity relationships. However, in most, if not all, biological systems, affinity is locally rather than globally determined. Interactions between substrate molecules and biological receptors are generally limited to contacts between isolated fragments of the receptor and the substrate surface. In this situation, analysis of global similarities between substrates is inappropriate as a method of developing structure-activity relationships, since only fragments of the substrate are directly involved in the generation of binding affinity.

Locally similar structures share similar structural fragments in similar relative positions and orientations. Locally similar structures are not necessarily globally similar. Sampling of molecular properties may be achieved by a total sampling strategy involving evaluation of global similarity; a fragment sampling strategy involving evaluation of local similarity; and multiple fragments sampling strategies involving evaluation of both local and global similarity.

The analysis of local similarities relies on sampling discrete regions of substrates for similar structures and charge distributions. In biological receptors, localized sampling arises due to the irregularity or bumpiness of the adjacent substrate and receptor surfaces. Interactions between closely opposed surfaces will predominant over interactions between more separated regions in the determination of binding affinity. The proximity of the adjacent surfaces will also determine the strength of hydrophobic binding. The effective simulated receptors generated by the present method must exploit discrete local sampling of target substrates (molecules) in order to evaluate functionally relevant similarities between compounds.

Analysis of local similarities is complicated by two factors: 1) the number, location and identity of the relevant fragments sufficient and necessary for specific binding affinity cannot usually be established by simple deduction from the chemical structure of the substrate; and 2) the positions and orientations of the sampled fragments are dependent upon the underlying structure of the whole molecule.

The part of the present method directed to the generation of simulated receptors capable of categorizing similarities between chemical substrates is essentially a search for receptors that sample the relevant fragments of the substrates at the relevant locations in space. The optimization process relies on four features of simulated receptors: 1) generality: wherein the receptors are able to bind with more than one substrate; 2) specificity: the binding affinity of the receptors varies with substrate structure; 3) parsimony: the receptors differentiate among substrates on the basis of a minimal set of local structural features; and 4) mutability: alteration of the structure of a receptor can change its binding affinity for a specific substrate. Encoding of the receptor phenotype in the form of a linear genotype represented by a character string facilitates the processes of mutation, recombination and inheritance of the structural characteristics of the simulated receptors.

Simulated receptors that satisfy these fundamental criteria can be optimized to obtain specific binding affinities for locally similar substrates using evolutionary selective breeding strategies. This is accomplished by encoding the spatial configuration and charge site distribution of the receptor in an inheritable format that can undergo alterations or mutations. Like biological receptors, the simulated receptors generated by this method define a three-dimensional exclusion space. Such a three-dimensional space can be outlined to an arbitrary degree of resolution by a one-dimensional path of sufficient length and tortuosity. Proteins formed from linear polymers of amino acids are examples of such structures. Similarly the three-dimensional structure of simulated receptors can be encoded as a linear array of turning instructions. This one-dimensional encoded form of the receptor constitutes its genotype. The decoded form used to assess binding affinity constitutes its phenotype. During the optimization process alterations (mutations) are made to the receptor genotype. The effects of these changes on the binding affinity of the phenotype are subsequently evaluated. Genotypes that generate phenotypes with desirable binding affinities are retained for further alteration, until, by iteration of the mutation and selection process, a selected degree of optimization of the phenotype is achieved. A variety of evolutionary strategies, including classical genetic algorithms, may be used to generate populations of simulated receptors with optimal binding characteristics.

Receptors generated by this method are then used to generate or identify novel chemical structures (compounds) which share the specific, useful properties of the molecular target species used as selection criteria in producing the simulated receptors. Using interaction with the receptors as selection criteria, novel chemical structures are evolved to optimally fit the receptors. Because these structures must meet the necessary and sufficient requirements for receptor selectivity, they are likely to also possess biological activity similar to that of the original molecular targets. The population of simulated receptors with enhanced selectivity may also be used to screen existing chemical structures for compounds with high affinity that may share these useful properties. The same process may also be used to screen for compounds with selected toxicological or immunological properties.

In one aspect of the invention there is provided a computer-based method of designing chemical structures having at least one preselected functional characteristic. The method comprises the steps of:

(a) providing a population of receptors having a preselected fitness coefficient for a set of target molecules sharing at least one quantifiable functional characteristic;

(b) providing a physical model of a chemical structure, calculating an affinity between the chemical structure and each receptor in a plurality of orientations using an effective affinity calculation, using the calculated affinity to calculate an affinity fitness score;

(c) altering the chemical structure to produce a variant of the chemical structure and repeating step (b); and (d) retaining and further altering those variants of the chemical structure whose affinity score approaches a preselected affinity score.

In this aspect of the invention the step of providing a physical model of said chemical structure may include providing a molecular character sequence encoding said chemical structure, and wherein the step of providing a population of receptors having a preselected fitness coefficient comprises at least;

(a) producing a physical model of a simulated receptor phenotype encoded in a linear character sequence, and providing a set of target molecules sharing at least one quantifiable functional characteristic;

(b) for each target molecule;
  (i) calculating an affinity between the receptor and the target molecule in each of a plurality of orientations using an effective affinity calculation;
  (ii) calculating a sum affinity by summing the calculated affinities;
  (iii) identifying a maximal affinity;

(c) using the calculated sum and maximal affinities to:
  (i) calculate a maximal affinity correlation coefficient between the maximal affinities and the quantifiable functional characteristic:
  (ii) calculate a sum affinity correlation coefficient between the sum affinities and the quantifiable functional characteristic;

(d) using the maximal correlation coefficient and sum correlation coefficient to calculate a fitness coefficient; and (e) altering the structure of the receptor and repeating steps (b) through (d) until a population of receptors having a preselected fitness coefficient are obtained.

In another aspect of the invention there is provided a method of screening chemical structures for preselected functional characteristics, comprising:

a) producing a simulated receptor genotype by generating a receptor linear character sequence which codes for at least spatial occupancy and charge;

b) decoding the genotype to produce a receptor phenotype, providing at least one target molecule exhibiting a selected functional characteristic, calculating an affinity between the receptor and each target molecule in a plurality of orientations using an effective affinity calculation, calculating a sum and maximal affinity between each target molecule and receptor, calculating a sum affinity correlation coefficient for sum affinity versus said functional characteristic of the target molecule and a maximal affinity correlation coefficient for maximal affinity versus said functional characteristic, and calculating a fitness coefficient dependent on said sum and maximal affinity correlation coefficients;

c) mutating the receptor genotype and repeating step b) and retaining and mutating those receptors exhibiting increased fitness coefficients until a population of receptors with preselected fitness coefficients are obtained; thereafter d) calculating an affinity between a chemical structure being screened and each receptor in a plurality of orientations using said effective affinity calculation, calculating an affinity fitness score which includes calculating a sum and maximal affinity between the compound and each receptor and comparing at least one of said sum and maximal affinity to the sum and maximal affinities between said at least one target and said population of receptors whereby said comparison is indicative of the level of functional activity of said chemical structure relative to said at least one target molecule.

In another aspect of the invention there is provided a method of designing simulated receptors mimicking biological receptors exhibiting selective affinity for compounds with similar functional characteristics, comprising the steps of:

a) producing a simulated receptor genotype by generating a receptor linear character sequence which codes for spatial occupancy and charge;

b) decoding the genotype to produce a receptor phenotype, providing a set of target molecules sharing similar functional characteristics, calculating an affinity between the receptor and each target molecule in a plurality of orientations using an effective affinity calculation, calculating a sum and maximal affinity between each target molecule and receptor, calculating a sum affinity correlation coefficient for sum affinity versus a functional characteristic for each target molecule and a maximal affinity correlation coefficient for maximal affinity versus said functional characteristic for each target molecule, and calculating a fitness coefficient dependent on said sum and maximal affinity correlation coefficients for each target molecule; and c) mutating the genotype and repeating step b) and retaining and mutating those receptors exhibiting increased fitness coefficients until a population of receptors with preselected fitness coefficients are obtained.

In another aspect of the invention there is provided a computer-based method of designing chemical structures having a preselected functional characteristic, comprising the steps of:

(a) providing a physical model of a receptor and a set of target molecules, the target molecules sharing at least one quantifiable functional characteristic;

(b) for each target molecule;

(i) calculating an affinity between the receptor and the target molecule in each of a plurality of orientations using an effective affinity calculation;

(ii) calculating a sum affinity by summing the calculated affinities;

(iii) identifying a maximal affinity;

(c) using the calculated sum and maximal affinities to:

(i) calculate a maximal affinity correlation coefficient between the maximal affinities and the quantifiable functional characteristic;

(ii) calculate a sum affinity correlation coefficient between the sum affinities and the quantifiable functional characteristic;

(d) using the maximal correlation coefficient and sum correlation coefficient to calculate a fitness coefficient;

(e) altering the structure of the receptor and repeating steps (b) through (d) until a population of receptors having a preselected fitness coefficient are obtained;

(f) providing a physical model of a chemical structure, calculating an affinity between the chemical structure and each receptor in a plurality of orientations using said effective affinity calculation, using calculated affinities to calculate an affinity fitness score;

(g) altering the chemical structure to produce a variant of the chemical structure and repeating step (f); and (h) retaining and further altering those variants of the chemical structure whose affinity score approaches a preselected affinity score.

In yet another aspect of the invention there is provided a method of encoding chemical structures comprising atomic elements, the method comprising providing a linear character sequence which codes for spatial occupancy and charge for each atom of said chemical structure.

BRIEF DESCRIPTION OF THE DRAWINGS

The method of the present invention will now be described, by example only, reference being had to the accompanying drawings in which.

DESCRIPTION OF THE PREFERRED EMBODIMENTS

Figure 1:
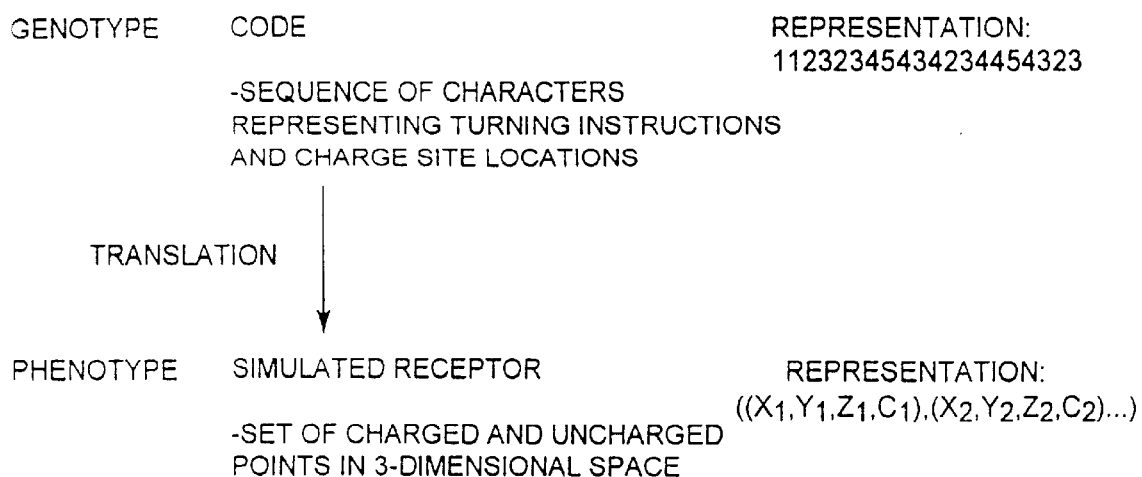
FIG. 1 is a flow chart showing relationship between genotype code creation and translation to produce a corresponding phenotype forming part of the present invention.

The method can be broken into two parts: (A) evolution of a population of simulated receptors with selective affinity for compounds with shared functional characteristics and (B) generation of novel chemical structures having the shared functional characteristics. Part (A) comprises several steps including 1) receptor genotype and phenotype generation; 2) presentation of the known chemical structure(s) to the receptor; 4) evaluation of affinity of the receptor for the chemical structure(s); 5) assessing the selectivity of the receptor for the chemical structure(s); 6) stochastically evolving a family of related receptors with optimized selective affinity for the chemical structure(s); screening chemical substrates for toxicological and pharmacological activity and using the optimized receptors to design novel chemical structure(s) with selective binding affinity for the receptors.

The following description of the best mode of the invention refers to various tables of molecular and atomic radius, polarizabilities, effective dipole values, and transition states and addition factors which values are found in Tables I to V located at the end of the description. Flowcharts giving non-limiting examples of process calculations are attached to the end of the description in Modules 1 to 15.

Part A: Evolution of Population of Simulated Receptors Exhibiting Selective Affinity for Target Molecules Sharing Commom Functional Characteristics

(1) Genotpe Code and Receptor Phenotype Generation

Both the simulated receptor genotypes and phenotype are computational objects. The phenotypes of the simulated receptors consist of folded, unbranched polymers of spherical subunits whose diameter is equal in length to the Van der Waals radius of atomic hydrogen ($\cong$110 pm). The radius of the hydrogen atom was chosen as the lower limit of spatial resolution. In many biological receptors, the majority of the receptor surface is formed by projecting hydrogen atoms. Subunits can be connected to each other at any two of the six points corresponding to the intercepts of the spheres with each of their principal axes. In the present implementation connections between subunits cannot be stretched or rotated and the centers of two connected subunits are always separated by a distance equal to the length of their sides (i.e. 1 hydrogen radius). Turns occur when two subunits are not attached to the opposite faces of their common neighbor. Four kinds of orthogonal turns are possible: left, right, up and down. Turns must be made parallel to one of the principal axes. For computational simplicity, if turns result in intersection with other subunits in the polymer, subunits are permitted to occupy the same space with other subunits.

A complete simulated receptor consists of one or more discrete polymers. In the case of receptors consisting of multiple polymers, the individual polymers can originate at different points in space. For computational simplicity, all polymers comprising a single receptor are chosen to be of the same length in this implementation (=number of subunits). This restriction is not a requirement for functionality, and sets of polymers differing in length may be useful for modelling specific systems.

The structure of each polymer is encoded as a sequential set of turning instructions. The instructions identify individual turns with respect to an internal reference frame based on the initial orientation of the first subunit in each polymer. Encoding on the basis of an internal reference frame mimics the assembly of proteins and ribozymes more closely than encoding on the basis of an external coordinate system.

Hydration of the receptor and substrate are not treated explicitly in the current implementation, instead, it is assumed that any water molecules present at the binding site are attached permanently to the receptor surface and comprise an integral part of its structure. This is an arbitrary approximation and those skilled in the art will appreciate that it could be replaced by a more exact treatment (see, for example, VanOss, 1995, *Molecular Immunology* 32:199–211).

With reference to FIG. 1, the code creation module generates random strings of characters. Each character represents either a turning instruction or determines the charge characteristics or reactivity of a point in the three-dimensional shape comprising the virtual receptor. A minimum of five different characters are required to create a string describing the three-dimensional shape of a receptor based on Cartesian (rectangular) coordinate framework. Other frameworks, e.g. tetrahedral structures can also be constructed using different sets of turning instructions. The characters represent turning instructions which are defined with respect to the current path of the virtual receptor structure in three-dimensional space (i.e. the instructions refer to the intrinsic reference frame of the virtual receptor and not an arbitrary external reference frame). An external reference frame is defined arbitrarily outside the receptor structure as a three-dimensional coordinate system (rectangular, cylindrical or spherical). The position of each subunit is specified by a triplet of coordinates (e.g. (x, y, z)) and turns are specified by the resulting unit changes to these coordinates. For example x, y, z $\rightarrow$ x, y+1, z+1 could specify a turn in an external rectangular coordinate system.

An intrinsic reference frame is defined with respect to the path of the polymer, and without reference to an external coordinate system. In place of turning instructions defined in terms of incremental changes in coordinates, turning instructions are given with respect to the current direction and orientation of the polymer. Only left, right, up and down turns are permitted. If a turn does not occur the polymer can either terminate or continue in its current direction. The virtual receptors generated in the current implementation are based upon an intrinsic reference frame.

While the receptor could be encoded using either an external or internal coordinate system, and codes can be interconverted, an internal coordinate system is preferred since the effects of mutation and recombination differ between coordinate systems. Particularly, mutations of codes based on external reference frames cause more restricted changes in phenotype architecture than similar mutations applied to codes based on internal reference frames. Specifically, the spatial orientations of the portions of the phenotype derived from unmutated sections of the code are unaffected (conserved) when the code is based on an external coordinate system. In contrast, the orientation of the portion of the phenotype distal to both the attachment site of the polymer and the mutation site will be affected by mutation if an internal reference frame is employed. As a result, the impact of point mutations on the receptor phenotype is generally greater when codes based on an internal reference frame are used. The three-dimensional tertiary structures of both proteins and ribozymes are partially based on internal reference frames (bond angles between adjacent peptides).

For a rectangular system the minimum character set is: $C_1$=no turn; $C_2$=right turn; $C_3$=left turn; $C_4$=up turn; and $C_5$=down turn. It will be understood that instructions could be combined to create diagonal turns e.g. $A_{1,2}=C_1C_2$; $A_{2,1}=C_2C_1$, etc. The number of different characters that determine different charge or reactivity states is unrestricted and may be adjusted according to empirical evidence. Codes may differ both in length (number of characters) and frequency with which specific characters appear in the series.

Example Of Genotype Creation

The following example of a genotype code creation and phenotype expression will be understood by those skilled in the art to be illustrative only. In this example the following conventions are employed.

(1) The character set used to generate the codes consists of five characters referring to turning instructions and two characters identifying a charged site: "0"=no turn; "1"=right turn; "2"=up turn; "3"=left turn; "4"=down turn; "5"=positively charged site (no turn); and "6"=negatively charged site (no turn).

(2) Subunits are of two types: charged or uncharged. All charged subunits are assumed to carry a unitary positive or negative charge. The uniform magnitude of charges is an arbitrary convention. It will be understood that receptors may also be constructed using subunits with different charges. The use of uniform charges in the present instance is a computational simplification. It also reduces the number of factors influencing the strength of electrostatic interactions between the receptor and substrate to two: the magnitude of the charge on the substrate; and the distance between the charge sites.

(3) The receptors comprise 15 discrete polymers. The length of the complete code is always a multiple of fifteen. The length of each polymer is equal to the total code length divided by fifteen. It will be understood that receptors can be constructed from any number of discrete polymers of varying or constant length.

(4) The following parameters are set by the user: (a) total code length (and polymer length); (b) the frequency with which each character occurs in the code string; and (c) the occurrence of character combinations. Module I gives a flowchart of a sample of genotype code creation.

Example of Receptor Phenotype Creation

Each genotype code is translated to create the three-dimensional description of its corresponding phenotype or virtual receptor. From a predefined starting point a translation algorithm is used to convert the turning instructions into a series of coordinate triplets which describe the position in space of the successive subunits comprising the receptor polymers. The starting coordinates for each polymer must be given prior to translation. The translation assumes that centers of successive subunits are separated by a distance equal to the covalent diameter of a hydrogen atom.

The translation algorithm reads the code string sequentially to generate successive turns and straight path sections. The interpretation of successive turns with respect to an external coordinate system depends upon the preceding sequence of turns. For each polymer comprising the receptor, the initial orientation is assumed to be the same.

In the current implementation, the translation algorithm is described by TABLE I giving the input and output states. If no turn occurs, the most recent values for $\Delta x, \Delta y, \Delta z$ and new state are used to calculate the new coordinate triplet. Charge sites are treated as straight (no turn) sections. The initial value of old state is 20.

The following parameters can be set by the user:
  a. Starting coordinates for each polymer comprising the receptor.
Output is stored as:
  a. Three vectors (one for each axes: $\{x_1, x_2, x_3 \ldots x_n\}$, $\{y_1 \ldots y_n\}$, $\{z_1 \ldots z_n\}$).
  b: A three-dimensional binary matrix.
  c. Separate vectors for charge site coordinates.

A sample process of code translation is give in module 2.

(2) Target Generation

Targets are represented as molecules consisting of spherical atoms. The atoms are considered to be hard spheres with fixed radii characteristic for each atomic species. The hard sphere radius at which the repulsive force between the target atoms and the virtual receptor is considered to be infinite is approximated by the exposed van der Waals radius given in TABLE 2. Other estimated values of the van der Waals radius can be used in place of those in TABLE 2.

The distance between the atomic centers of two atoms connected by a covalent bond is expressed as the sum of their covalent bond radii. Covalent bond radii vary with bond order and atomic species. Examples of suitable values of bond radii are given in TABLE 3. As a first approximation, bond length is assumed to be fixed (i.e. bond vibrations are ignored). Bond rotation is permitted, and multiple configurations of the same structure are required to sample representative rotational states. Configurational stability is not considered because binding with the virtual receptor may stabilize otherwise energetically unstable configurations. Various energy minimization algorithms can be applied to the generation of target ligands.

Electrical charges arising due to bond dipole moments are considered to be localized at the atomic nuclei. The negative charge is carried by the atom with the larger electronegativity. The dipole values used in the current implementation are given in TABLE 4.

(3) Target Presentation

The affinity of the each target for the simulated receptor(s) is tested for several orientations of the target relative to the upper surface of the receptor. The upper surface is defined by the translation algorithm. Prior to the evaluation of binding affinity, the target and receptor must be brought into contact. Contact occurs when the distance between the centers of at least one subunit of the receptor and at least one atom of the target is equal to their combined radii. In order to determine the relative positions of the target and receptor at the point of contact, the target is shifted incrementally towards the receptor surface along a path perpendicular to the surface and passing through the geometric centers of both the receptor and the target. When contact occurs, the target has reached its collision position relative to the receptor. The translated positions of the target atoms when the collision position is reached are used to calculate distances between the atoms of the target and the subunits of the receptor. These distances are used to calculate the strength of electrostatic interactions and proximity.

In the current implementation, the target is assumed to travel in a straight line towards the receptor, and to retain its starting orientation at the time of contact. An alternative approach would allow the target to incrementally change its orientation as it approached the receptor so that the maximal affinity position was achieved at the point of contact. Although this method is functionally similar to that implemented, it is much more computationally complex. In the current implementation, multiple orientations are tested at lower computational effort. The current implementation allows for adjustable displacement of the path along the x and/or y axis of the receptor to accommodate larger molecules. This feature is required to enhance selectivity when molecules differing in size are tested on the same receptor.

Prior to the calculation of the collision position, the orientation of the target is randomized by random rotation in 6° increments around the x, y, and z axes. Each of these random orientations of the target is unique in a given test series. The reliability of the optimization process is dependent upon the number of target orientations tested as well as the number of target compounds evaluated. A sample process for target presentation is given in Module 4.

(4) Calculation of Affinity

Approximation Strategy

An exact calculation of the interaction energy between the targets and virtual receptor is neither practical nor desirable. The optimization of the simulated receptors requires multiple testing of numerous target-receptor pairs. The number of pairs tested per unit time is dependent on the time required to evaluate the affinity of each pair. Although the use of more accurate affinity calculations may result in greater discriminatory capacity, this gain will be at the price of increased computational effort. Furthermore, some components of the total interaction energy do not yet have an exact quantitative treatment, for example hydrogen bonding and hydrophobic interactions. The current implementation is based on a simplified approximation that evaluates the principal components of affinity with relatively little computational effort. The approximation is developed in the following sections. However, it will be appreciated by those skilled in the art that more exact affinity calculation procedures may be utilized which give a more exact affinity value. Known computational packages for calculating more accurate affinity values may be used directly in the present process.

Quantitative evaluation of the electrostatic interactions between receptor and ligand (or host and guest molecular complexes) requires a detailed description of the electron density distributions of the interacting molecules. However, in general the size of the molecules involved, particularly polypeptides, makes ab initio calculations of the electronic structure very difficult. This problem is often aggravated by the large number of torsional degrees of freedom and lack of knowledge concerning the conformations of the interacting molecules during binding.

Studies of crown ethers indicate that the electron density distribution of small molecules can be used to describe the electron densities of larger compounds (Bruning, H. And Feil, D. (1991) J. Comput. Chem. 12: 1). Hirshfeld's stockholder method can be used to define strictly local charge distributions that are subsequently characterized by charge and dipole moment (Hirshfeld, F. L. (1977) Theor. Chim. Acta 44: 129). The result is the division of the total electron density distribution of the molecule into overlapping atomic parts, the sizes of which are related to the free atomic radii.

Unfortunately these methods do not yield reliable values for binding energies and are largely restricted to electrostatic interactions that can be derived from electron density distributions. However, it is possible to demonstrate in crown ethers that the major components of electrostatic interactions are determined by local rather than global transfers of charge between atoms. Charge distribution is mainly determined by short range effects due to different chemical bonds. In particular, non-neighboring atoms contribute little to atomic dipole moments. In addition, although charge transfer between atoms is also influenced by the electrostatic field of the whole molecule, calculations for crown ethers show only a very small influence on the charge distribution.

Calculated stockholder atomic charges and dipole moments can be used to describe electrostatic interactions (Bruning, H. And Feil, D. (1991) J. Comput. Chem. 12: 1). Beyond the van der Waals radius there is only a minor contribution from the atomic quadrapole moments. Calculations of the electrostatic potential that take only atomic charges into account give very poor results, whereas use of the dipole moments generates improved values.

Based on these considerations, the method of the present invention incorporates an approximation of affinity between the target ligand and the simulated receptor(s) and between the simulated receptor(s) and chemical structure(s) being designed based on two measures.

1. The magnitude of the electrostatic forces generated between the charged subunits of the simulated receptor(s) and the atomic dipoles of the target ligand (chemical structure). Because the charged subunits are assumed to carry non-transferrable unit charges, the magnitude of these forces is directly proportional to the magnitude of the atomic dipole and inversely proportional to the distance between the simulated receptor and the atomic dipole of the ligand.

2. The proportion of the non-polar or uncharged subunits of the simulated receptor sufficiently close to the non-polar regions of the ligand for the generation of significant London dispersion forces.

Assumptions Used For Affinity Calculation in the Current Implementation:

1. The chemical substrate targets evaluated by the current implementation are assumed to be neutral (i.e. not ionized) molecules. This is an arbitrary limitation, and an implementation applicable to charged and uncharged targets can be developed using the same methodology.

2. The dipole moments are assumed to be localized at the atomic nuclei. A similar analysis of affinity could be made assuming the dipole moment to be centered on the covalent bond. According to Allingham et al. (1989), these assumptions are functionally equivalent.

3. The environment surrounding the virtual receptor is assumed to be a solvent system in which the target occurs as a solute. The target is effectively partitioned between the solvent and the virtual receptor.

4. At the instant for which the affinity is calculated, the target and receptor are assumed to be stationary with respect to each other, and in a specific, fixed orientation.

5. The targets are assumed to interact with only two types of site on the receptor surface: fixed charge sites (either negatively or positively charged) and non-polar sites.

On the basis of these assumptions, it is only necessary to consider the following contributions to the strength of the interaction:

1. Charge-Dipole $-Q^2\mu^2/6 (4\pi\epsilon)^2 kTr^4$
2. Charge-Non-polar $-Q^2\alpha/2 (4\pi\epsilon)^2 r^4$
3. Dipole-Non-polar (Debye energy) $-\mu^2\alpha/(4\pi\epsilon)^2 r^6$
4. Non-polar-Non-polar (London energy) $-0.75[h\nu\alpha^2/(4\pi\epsilon)^2 r^6]$ In the current implementation, only relative strengths are considered by the approximation, therefore all constants are ignored. In addition the fixed charge site is assumed to be unitary and either positive or negative. On this basis, the four components can be rewritten in simplified form:

1. Charge-Dipole $-\mu^2/r^4$ or $-\mu/r^2$
2. Charge-Non-polar $-\alpha/r^4$
3. Dipole-Non-polar (Debye energy) $-\mu^2\alpha/r^6$ or $-\mu\alpha^{0.5}/r^3$
4. Non-polar-Non-polar (London energy) $-\alpha^2/r^6$ or $-\alpha/r^3$ In general, terms 2 and 3 make only small contributions to long-range interactions. However, both 1 and 4 contribute significantly to the interaction energy. In the current implementation, most interactions between non-polar fragments are assumed to occur between adjacent alkyl and aromatic hydrogens and the non-polar subunits of the receptor. Under these conditions the value of $\alpha$ is assumed to be approximately constant.

Hydrophobic Strength and Water Exclusion Contribution

Solvation effects are important considerations in the generation of binding affinity. For example, hydrophobic bond formation relies upon the close spatial association of non-polar, hydrophobic groups so that contact between the hydrophobic regions and water molecules is minimized. Hydrophobic bond formation may contribute as much as half of the total strength of antibody-antigen bonds. Hydration of the receptor and substrate surfaces is also a significant factor. Water bound to polar sites of either the receptor or substrate surface can interfere with binding or increase affinity by forming cross-bridges between the surfaces.

The hydrophobic interaction describes the strong attraction between hydrophobic molecules in water. In the case of receptor-target interactions it is taken to refer to the attraction between the non-polar fragments of the target and adjacent domains of non-polar receptor subunits. The effect arises primarily from entropic effects resulting in rearrangements of the surfaces so that water is excluded between adjacent non-polar domains. Exact theoretical treatments of the hydrophobic interaction are unavailable, however, it is estimated that hydrophobic forces contribute as much as 50% of the total attraction between antibodies and antigens. In order to estimate the hydrophobic interaction between targets and virtual receptors, the present implementation evaluates the proportion of the receptor that is effectively shielded from solvation by binding with the target. All non-polar (uncharged) subunits that are within a fixed distance of non-polar atoms on the target are considered to be shielded from solvation by solvent molecules of diameter equal to or greater than the limiting distance.

Combined Affinity Calculation

The combined affinity calculation used in the current implementation combines two measures of interaction: the summed strengths of the charge-dipole interactions and a proximity measure. These affinities are assumed in the current implementation to be isotropic. It will be appreciated by those skilled in the art that greater discriminatory power may be obtained if anisotropic calculations of affinity are used, although these are computationally much more complex.

The charge-dipole interaction is calculated as $D = \Sigma \mu_i / r_{ij}^v$, where $\mu_i$=the dipole moment of the ith atom of the target and $r_{ij}$=the distance between the ith atom and the jth charge site on the receptor, and the coefficient v can be set to 2, 3, or 4. The contribution of D to the total affinity is more sensitive to charge separation for larger value of v.

The proximity measure is calculated as $P = \Sigma n_i / N$, where $n_i$=the number of uncharged subunits of the receptor that are separated by a maximum distance of $\delta$ from the ith atom of the target with a dipole moment $\leq 0.75$ Debye. In the current implementation, $\delta$ can range from 1 to 4 subunit diameters (this approximates the van der Waals radius of water). N is the total number of subunits comprising the receptor.

An affinity value A is calculated from D and P using the following relationship $A = [P(D+NP/k)]^{0.5}$, where k is a fitting constant (in the current implementation, k=10000). The value of P in the equation serves two roles. In the first instance it is a weighting factor. As a measure of "goodness of fit" it is use to bias the affinity value in favor of those configurations in which the non-polar regions of the target and receptor are in close contact. Under these conditions, hydrophobic interactions and non-polar interaction energies will be large and will contribute significantly to the stability and strength of the bond. Under these conditions the target has fewer possible trajectories to escape from the receptor and its retention time will be prolonged. In the second instance P is used to estimate the contribution of the dispersion energy to the strength of the interaction. It is assumed that the dispersion energy will only be significant for uncharged, non-polar regions, and that it is only significant when the target and receptor are close to each other (i.e. within $\delta$ of each other). The values of k and $\delta$ can be adjusted to alter the relative contribution of P and D. In general, P dominates for non-polar targets, whereas D is more significant for targets with large local dipoles. Hydrogen bonding is approximated by paired negatively and positively charged receptor units interacting simultaneously with target hydroxyl, carboxylic or amine functional groups.

Alternative Approaches to Affinity Calculation-Bond Polarizability

It may be advantageous is certain cases to introduce a parameter corresponding to the relative polarizability of the target atoms into the affinity calculation. In this case the equation for calculating $P_2$ in $A = [P(D+NP_2/k)]^{0.5}$ is not $P_2 = \Sigma n_i / N$. Instead, $P_2$ is calculated as $P_2 = \Sigma \alpha_i n_i / N$; where $n_i$=the number of either charged or uncharged subunits of the receptor that are separated by a maximum distance of $\delta$ from the ith atom of the target and $\alpha_i$ is the relative polarizability of the ith atom of the target. For simplicity $\alpha_H$ could be set to 1.0 for aliphatic hydrogen. The value of k must be adjusted if polarizabilities are used. Sample polarizabilities based on the sums of adjacent bond polarizabilities are given in TABLE V.

Since polarizability is associated with displacement of the electron cloud, the polarizability of a molecule can be calculated as the sum of the characteristic polarizabilities of its covalent bonds. This additivity holds for non-aromatic molecules that do not have delocalized electrons.

Alternative Techniques-Functional Group Specificity

The affinity approximation used in the current implementation could be replaced by functionally similar computations that preserve the relationship between local charges, dispersion energy and target-receptor separation. In addition, affinity measures for charged targets could be constructed. The present implementation evaluates only non-covalent interactions, however, the method could be expanded by including in the virtual receptor subunits capable of specific covalent bond-forming reactions with selected target functional groups. Module 5 provides a sample flowchart of the preferred effective affinity calculation used in the present invention.

(5) Assessment of Selective Affinity

Figure 2:
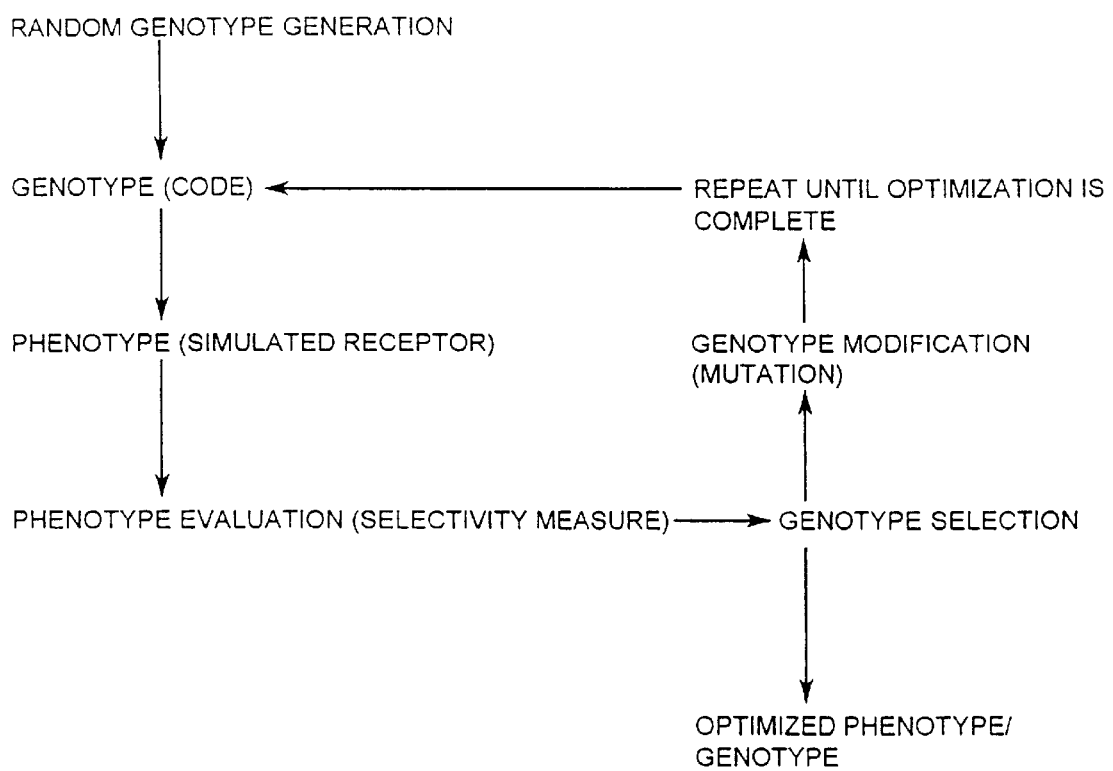
FIG. 2 is a flow chart showing an overview of the steps in the optimization of a receptor for selectively binding to a set of substrates using point mutations forming part of the present invention.
Figure 3:
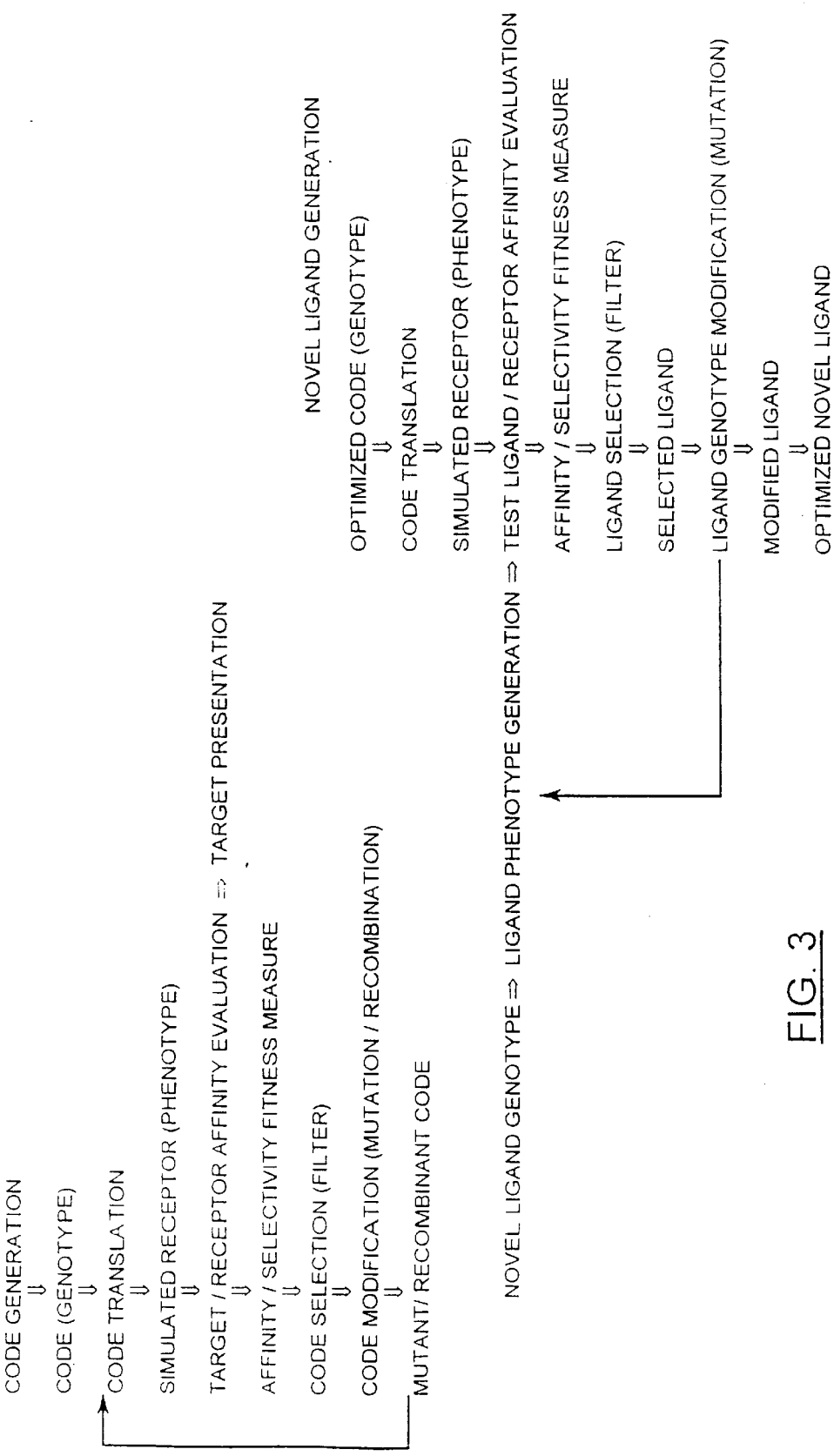
FIG. 3 is a flow chart showing an overview of the steps in the process of producing a population of related receptors with optimized selective binding affinity for a set of chemical substrates and using these optimized receptors for producing a set of novel chemical substrates with common shared functional characteristics.

Goodness of fit between a virtual receptor and a set of target substrates is evaluated by comparing the known activity or affinity values for the targets with those obtained for the virtual receptor-target complex. The maximal affinities of an optimally selective virtual receptor should be strongly correlated with known affinity measures. Successive iterations of point mutations can be used to enhance this correlation between a set of substrates and a virtual receptor (FIG. 2) or for optimizing selectivity of a population of virtual receptors successive iterations of the evolutionary process may used to enhance this correlation (FIG. 3).

Known values can be any index known or suspected to be dependent upon binding affinity, including (but not limited to) $ED_{50}$, $ID_{50}$, binding affinity, and cohesion measures. The values tested must be positive. Logarithmic transformation of the data may be required. Unweighted rank data cannot be used.

The optimal orientation of the targets for maximal binding affinity is unknown prior to testing. In order to obtain a representative measure of the range of receptor-target affinity, each target must be tested repeatedly using different random orientations relative to the receptor surface. Each test uses Module 5 to evaluate affinity. In general, the reliability of the maximal affinity values obtained depends upon the sample size, since it becomes increasingly likely that the sample will contain the true maximal value. The same set of target orientations is used for testing each receptor.

Two techniques are employed in the current implementation to circumvent the need for large sample sets for the generation of optimized receptors: 1) the use of a measure combining average (or sum) affinity and maximal affinity to select for receptors with higher selectivity; and 2) incremental increases in the number of orientations tested with successive iterations of the optimization process (optimization begins with a small set of target orientations, as receptors of greater fitness are generated, more orientations are tested).

In the current implementation, the sum is calculated for the affinity values obtained for all the tested orientations of each target. This sum affinity score is a measure of the average affinity between the receptor and the target. At the same time, the maximal affinity value is also determined.

Correlations between the known values and both the sum affinity $r_{SA}^2$ and the maximal affinities $r_{MA}^2$ are calculated.

The origin (0,0) is included in the correlation, based on the assumption that target compounds showing no activity should have little or no affinity for the virtual receptor. This assumption may not always be valid, and other intercept values may be required in some tests.

The correlation of using sum affinity is a measure of the average goodness of fit. If this correlation is large, but the correlation between maximal affinity and known affinity is weak, the result suggests that the virtual receptor is not selective, i.e. multiple orientations of the target can interact effectively with the receptor. Conversely, if the maximal affinity is highly correlated with known affinity values and the correlation with sum affinity is weak, the virtual receptor my be highly selective. If both sum affinity and maximal affinity are highly correlated with known affinity, it is probable that the orientations sampled have identified the response characteristics of the receptor with limited error (both type I and type II errors are reduced: the likelihood of either a false positive or false negative result). In some cases it may be more appropriate to minimize the correlation between the known affinities and the sum affinity, while selecting for an increased correlation between maximal affinity and known affinity. Such a selection would require subtraction of the maximal affinity values from the sum total in order to remove these values as a source of confounding bias.

In the current implementation, a joint correlation value is used as the basis for receptor selection. This value is calculated as the square root of the product of the sum affinity and maximal affinity $$F = (r_{MA}^2 \times r_{SA}^2)^{0.5}$$

This value is optimized by the evolutionary process applied to the virtual receptors Note: If $r_{MA}^2$ and $r_{SA}^2$ are strongly correlated with each other, then the values contributing to $r_{SA}^2$ must either individually correlate closely with the maximal affinity value or contribute negligibly to the sum. Alternatively the correlation $(r_{SA-MA})$ for the (sum affinity—the maximal affinity) vs known affinity can be calculated and the measure $$F = (r_{MA}^2 \times (1 - r_{SA-MA}^2))^{0.5}$$

is maximized. Use of this measure will select for receptors that have high affinity for a very limited set of target orientations. Module 6 provides a flowchart of a sample goodness of fit calculation.

(6) The Optimization Process

The objective of the optimization process is to evolve a virtual receptor that has selective affinity for a set of target receptors. A highly efficient mechanism for finding solutions is required, since the total number of possible genotypes containing 300 instructions is $7^{300}$ or about $10^{253}$. The following four phases summarize the steps in the optimization process whereinafter each phase is discussed in more detail and example calculations given.

PHASE 1: Generate a set of random genotypes and screen for a minimal level of activity. Use selected genotype as basis for further optimization using genetic algorithm (recombination) and unidirectional mutation techniques.

PHASE 2: Mutate selected genotype to generate a breeding population of distinct but related genotypes for recombinations. Chose most selective mutants from population from population for recombination.

PHASE 3: Generate new genotypes by recombination of selective mutants. Select from the resulting genotypes those with the highest affinity fitness. Use this subpopulation for the next recombinant or mutation generation.

PHASE 4: Take best recombination products and apply repeated point mutations to enhance selectivity.

Phase I: Evolution-generation of Primary Code

The Genetic Algorithm developed by Holland (Holland, J. H. (1975) Adaptation in Natural and Artificial Systems. U. Michigan Press. Ann Arbour) can be used to search for optimal solutions to a variety of problems. Normally this technique is applied using large, initially random sets of solutions. In the present implementation the technique is significantly modified in order to reduce the number of tests and iterations required to find virtual receptors with high selectivity. This has been accomplished by using a set of closely related genotypes as the initial population and the application of high rates of mutation at each iteration. For any set of target compounds it is possible to develop distinct receptors with optimal affinity characteristics. For example, receptors may bind optimally to the same targets but in different orientations. The use of an initial population of closely related genotypes increases the likelihood that the optimization process is converging on a single solution. Recombination of unrelated genotypes, although it may generate novel genotypes of increased fitness, is more likely to result in divergence.

The objective of the first stage in the optimization process is to generate a genotype with a minimal level of affinity for the target set. This genotype is subsequently used to generate a population of related genotypes. A flowchart of a sample process for generation of a genotype with a minimum level of affinity is given in Module 7.

Phase 2: Evolution-Mutation of Primary Code

Mutation of the genotype comprises changing one or more characters in the code. Mutations in the current implementation do not alter the number of subunits comprising the receptor polymers and do not affect the length of the genotype. It will be appreciated that these conventions are arbitrary, and it will be understood that variants may have utility in some systems.

Mutations can alter the folding pattern of the phenotype, with resulting changes in the receptor shape space and the location or exposure of binding sites. Mutations that affect the configuration of peripheral regions of the phenotype can result in shifts of the receptor center relative to the target center.

Neutral Mutations

All mutations alter the structure of the phenotype, however, not all mutations result in changes in the functionality of the receptor. Such neutral mutations may alter components of the receptor that do not affect affinity. In some cases these neutral mutations can combine with subsequent mutations to exert a synergistic affect.

The Breeding Population

The objective of the second phase of the evolutionary process is the generation of a population of distinct but related genotypes derived from the primary genotype. Members of this population are subsequently used to generate recombinants. This breeding population is created by multiple mutation of the primary genotype. The resulting genotypes are translated and screened for selectivity. The most selective products are retained for recombination. Module 8 gives a flowchart for a sample process for multiple mutation of a genotype.

Phase 3: Evolution-Recombination

The objective of recombination is the generation of novel genotypes with increased fitness. Recombination facilitates the conservation of genotype fragments that are essential for phenotypic fitness, while at the same time introducing novel combinations of instructions. In general, recombination coupled with selection results in rapid optimization of selectivity. Module 9 gives a flowchart for a sample process for multiple mutation of a genotype.

The current implementation retains the population used for recombination for testing in step 7 of Module 9. This ensures that genotypes with high selectivity are not replaced by genotypes with lower selectivity. In addition, in the current implementation, mutations (Module 7) are applied to 50% of the recombinant genotypes prior to testing (Step 7-module 9). This step increases the variability within the recombinant population. The test populations used in the current implementation range in size from 10 to 40 genotypes. This is a relatively small population size. Under some conditions, larger populations may be required.

Phase 4: Evolution-Maturation

Progressive Micromutation Technique

The final stage in the optimization process mimics the maturation of antibodies in the mammalian immune system. A series of single point mutations are applied to the genotype, and the effect on phenotypic fitness is evaluated. Unlike recombination, this process generally results in only small incremental changes to the selectivity of the phenotype. The maturation process uses a Rechenberg (1+1) evolutionary strategy (Rechenberg, I. (1973), Evolutionsstrategie. F. Frommann. Stuttgart). At each generation the fitness of the parental genotype is compared to that of its mutation product, and the genotype with the greater selectivity is retained for the next generation. As a result, this process is strictly unidirectional, since less selective mutants do not replace their parents.

During each iteration of the maturation process, only a single instruction in the code is changed. If a parent and its mutation product have the same selectivity, the parent is replaced by its product in the next generation. This method results in the accumulation of neutral mutations that may have synergistic effects with subsequent mutations. This convention is arbitrary. Module 10 provides a flowchart for a sample maturation process.

If recombination or maturation do not generate improved selectivity after repeated iterations, it may be necessary to repeat Phase 2 in order to increase the variability of the breeding population genome.

Alternative Methods of Generating Receptor Populations

Those skilled in the art will appreciate that functionally similar or equivalent receptor populations may be constructed by alternative methods that generate similar selectivity and affinity scores based on the same structural criteria. These criteria include steric factors such as fit and hindrance, and the strength of electrostatic interactions. Computationally similar or equivalent approaches include the use of optimization processes such as neural networks and multivariate polynomial regression. Such methods could be applied to generate suitable receptor populations provided they collect structural data similar to that used in the preferred method described above to construct functionally equivalent classifier or object recognition algorithms.

Selected Applications

The process of the present invention can be used in several areas including: 1) screening for compounds with selected pharmacological or toxicological activity; and 2) development of novel chemical structures with selected functional characteristics. Both applications and examples are provided hereinafter.

1A) Screening Method

A population of receptors that have been evolved for selective affinity for a specific group of compounds sharing similar pharmacological properties can be used as probes for the identification of other compounds with similar activity, provided this activity is dependent upon binding affinity. For example, a population of receptors could be evolved to display specific affinity for salicylates. If the affinity of these receptors for salicylates closely correlates with the affinity of cyclooxygenase for salicylates, the receptors must at least partially mimic functionally relevant features of the binding site of the cyclooxygenase molecule. These receptors can therefore be used to screen other compounds for possible binding affinity with cyclooxygenase.

This technique can also be applied to screening compounds for potential toxicological or carcinogenic activity. For example, receptors could be evolved that mimic the specific binding affinity of steroid hormone receptors. These receptors could then be used to evaluate the affinity of pesticides, solvents, food additives and other synthetic materials for possible binding affinity prior to in vitro or in vivo testing. Simulated receptors may also be constructed to detect affinity for alternate target sites, transport proteins or non-target binding.

1B) Screening For Sub-Maximal Activity

In some instances compounds with high affinity may have deleterious side effects or may be unsuitable for chronic administration. In this case, compounds with lower binding affinity may be required. Techniques such as combinatorial synthesis do not readily generate or identify such compounds. In contrast, simulated receptors could be used to effectively screen for structures that display binding affinity of any specified level.

1C) Measuring Molecular Similarity

The selectivity of the simulated receptors can be used as a quantitative measure of molecular similarity.

Example of a Softare Implementation

Appendices A, B, and C are attached. Appendix A is a computer program written in Microsoft Visual Basic 3.0 which can be used to generated simulated receptors. Appendix B is a computer program, also written in Microsoft Visual Basic 3.0, which can be used to generate chemical structures. Appendix C is a file which is required to run both programs.

Both programs are merely examples of programs which can be used to carry out a particular implementations of the invention. Those skilled in the art can write other programs which can be used to practice the methods of the invention.

Examples of Simulated Receptors

In the examples, fictitious test values of target affinities were chosen to demonstrate the ability of the receptor generation program to construct simulated receptors mimicking any arbitrarily chosen pattern of activity.

In these examples, all receptors consist of 15 polymers. Width, Length, and Depth values specify origin coordinates of the 15 polymers relative to the center of the receptor.

EXAMPLE 1

A simulated receptor was generated with the following specifications:

Number of subunits: 240; Width: 6; Length: 6 Depth: 25

Code:

"4100033103212204103333424052312013341024124022232334010032242510144051332434003246204121001313100431121011324120224213024132311243301331003230523000433414010202230214041444350265203413103310220514141410214021340143100102311103312352100162440"

Each target was tested 20 times against the receptor The affinity score for the optimized receptor was 0.9358 which is relatively low.

The target substrates used to optimize the receptor were benzene, phenol, benzoic acid and o-salicylic acid. The aspirin precursor o-salicylic acid is an inhibitor of prostaglandin synthesis by cyclooxygenase. Benzoic acid and phenol have much lower affinity for the same site. The target affinity values and the scores for the receptor are shown in Table A below which shows that the simulated receptor has maximal affinity for o-salicylic acid.

| Target Compound | Target Affinity | Sum Affinity Score | Maximal Affinity Score |
| --- | --- | --- | --- |
| Benzene | 0.6 | 20.88 | 3.38 |
| Phenol | 1.2 | 8.03 | 4.99 |
| Benzoic Acid | 1.6 | 42.23 | 12.98 |
| o-Salicylic Acid | 4.4 | 80.33 | 34.71 |

Three test substrates were evaluated using the simulated receptor. Two of the compounds are known to be less active than o-salicylic acid: m-salicylic acid and p-salicylic acid. The third compound, Diflusinal is a fluorinated salicylic acid derivative of efficacy equal to or greater than that of salicylic acid. The results of the evaluation are given in Table B.

| Target Compound | Sum Affinity Score | Maximal Affinity Score |
| --- | --- | --- |
| m-Salicylic acid | 45.9 | 12.3 |
| p-Salicylic acid | 63.5 | 27.5 |
| Diflusinal | 117 | 71.2 |
| o-Salicylic Acid | 80.33 | 34.71 |

The results obtained using the simulated receptor closely match the pharmacological data for these compounds: m-salicylic acid and p-salicylic acid have lower affinity scores than o-salicylic acid and diflusinal is more active than o-salicylic acid. Further refinement of the simulated receptor and the use of additional, independently optimized receptors would be required to increase the certainty of these predictions of activity.

EXAMPLE 2

Simulated receptors selective for Benzodiazepams (Valium analogues).

Code:
"313305423414342402400322214113114321411360531
202421102432023
311101331100402112303321433140233044251241
2144202035124222313
1400221121332232410014212004131210231224143
02231344123301021 3"

Code Length: 180

Depth: 25 Width: 6 Length: 7

Number of Tests: 40

Population Size for Recombination: 10

Translation Factor: +/−2

Optimized Correlation Score: 0.98

Training Targets (used to optimize receptor affinity and selectivity; the target affinity scores are fictitious):

| Compound | Target Affinity | Sum Score | Maximal Affinity Score | |
| --- | --- | --- | --- | --- |
| Benzene | 0.5 | 64 | 7.5 | (inactive) |
| Diazepam | 8.5 | 616 | 263 | |
| Chlorodiazepam | 5.6 | 383 | 139 | (less active than Diazepam) |
| Methyldiazepam | 4.2 | 354 | 147 | (less active than Diazepam) |

Test Targets: (Small molecules not known to interact with the diazepam receptor):

| Compound | Sum Affinity Score | Maximal Affinity Score |
| --- | --- | --- |
| Phenol | −67.7 | 5.6 |
| Benzoic Acid | 198 | 31 |
| o-Salicylic Acid | 168 | 21 |

EXAMPLE 2a

A simulated receptor mimicking affinity of cyclooxygenase for salicylates.

Optimized Correlation Score: 0.95

Training Targets used to optimize selective affinity (Cyclooxygenase as receptor): These targets differ in affinity for cyclooxygenase. The target affinities used are fictitious.

| Compound | Target Affinity | Sum Affinity Score | Maximal Affinity Score |
| --- | --- | --- | --- |
| Benzene | 0.9 | 29.5 | 5.8 |
| Phenol | 1.6 | 21.0 | 7.4 |
| Benzoic Acid | 2.1 | 59.3 | 27 |
| o-Salicylic Acid | 5.3 | 134 | 105 |

Test Targets: (Both m-salicylic acid and p-salicylic acid should be less active than o-Salicylic acid)

| Compound | Affinity Sum | Maximal Score | Affinity Score | |
| --- | --- | --- | --- | --- |
| o-Salicylic Acid | 134 | 105 | | |
| m-Salicylic Acid | 52 | 28 | (less active) | |
| p-Salicylic Acid | 28 | 4 | (less active) | |

Note ordering of scores ortho>meta>para

EXAMPLE 2b

A simulated receptor mimicking affinity of cyclooxygenase for salicylates.

Optimized Correlation Score: 0.98

Training Targets used to optimize selective affinity (Cyclooxygenase as receptor): These targets differ in affinity for cyclooxygenase. The target affinities used are fictitious.

| Compound | Target Affinity | Sum Affinity Score | Maximal Affinity Score |
|---|---|---|---|
| Benzene | 1.1 | 15 | 2.4 |
| Benzoic Acid | 3.0 | 43.6 | 8.0 |
| o-Salicylic Acid | S.1 | 57.9 | 16.2 |

Test Targets: (Both m-salicylic acid and p-salicylic acid should be less active than o-Salicylic acid and Diflusinal is an active o-salicylate analogue)

| Compound | Sum Affinity Score | Maximal Affinity Score | |
|---|---|---|---|
| o-Salicylic Acid | 57.9 | 16.2 | |
| m-Salicylic Acid | 37.7 | 8.0 | (less active) |
| p-Salicylic Acid | 35.4 | 4.4 | (less active) |
| Diflusinal | 87.5 | 14.1 | (similar activity) |

Note ordering of scores ortho>meta>para

EXAMPLE 2c

A simulated receptor mimicking affinity of cyclooxygenase for salicylates.

Optimized Correlation Score: 0.98

Training Targets used to optimize selective affinity (Cyclooxygenase as receptor): These targets differ in affinity for cyclooxygenase. Phenol was not used in this optimization. The target affinities used are fictitious.

| Compound | Target Affinity | Sum Affinity Score | Maximal Affinity Score |
|---|---|---|---|
| Benzene | 1.1 | 15 | 2.4 |
| Benzoic Acid | 3 | 43.6 | 8 |
| o-Salicylic Acid | 5.1 | 57.9 | 16.2 |

Test Targets: (Both m-salicylic acid and p-salicylic acid should be less active than o-Salicylic acid, Diflunisal is as potent as o-Salicylic acid)

| Compound | Sum Affinity Score | Maximal Affinity Score | |
|---|---|---|---|
| o-Salicylic Acid | 57.9 | 16.2 | |
| m-Salicylic Acid | 37.7 | 8 | (less active) |
| p-Salicylic Acid | 35.4 | 4.4 | (less active) |
| Diflunisal | 87.5 | 14.1 | (similar activity) |

Note ordering of scores ortho>meta>para

EXAMPLE 3

A simulated receptor with stereospecific affinity for salicylates.

Optimized Correlation Score: 0.98

Training Targets used to optimize selective affinity (Cyclooxygenase as receptor):
These targets differ in affinity for cyclooxygenase. Phenol was not used in this optimization. In this example p-salicylate was assumed to have higher affinity than o-salicylate. The target affinities used are fictitious.

| Compound | Target Affinity | Sum Affinity Score | Maximal Affinity Score |
|---|---|---|---|
| Benzene | 0.9 | 11 | 26.3 |
| o-Salicylic Acid | 2.5 | 48.3 | 40.1 |
| p-Salicylic Acid | 6.2 | 94.8 | 83.8 |

Test Targets:

| Compound | Sum Affinity Score | Maximal Affinity Score | |
|---|---|---|---|
| p-Salicylic Acid | 94.8 | 83.8 | |
| m-Salicylic Acid | 68.7 | 61.3 | (less active) |
| Benzoic Acid | 73.5 | 63.5 | (less active) |
| Phenol | 31.5 | 32.6 | (less active) |

Note ordering of scores ortho<meta<para, which reverses the order shown in previous example.

EXAMPLE 4

A simulated receptor with specific affinity for salicylates. This receptor responds equally well to diflunisal and o-Salicylic acid, mainly on the basis of the benzoic acid moiety. It is not strongly specific, probably because of the very small set of optimization criteria used to generate it.

Optimized Correlation Score: 0.97

Training Targets used to optimize selective affinity (Cyclooxygenase as receptor): These targets differ in affinity for cyclooxygenase. Phenol and benzoic acid were not used in this optimization. In this example o-salicylate and diflunisal were assumed to have similar affinities. The target affinities used are fictitious.

| Compound | Target Affinity | Sum Affinity Score | Maximal Affinity Score |
|---|---|---|---|
| Benzene | 0.6 | 80 | 24 |
| o-Salicylic Acid | 7.4 | 232 | 122.3 |
| Diflunisal | 6.6 | 236 | 121.5 |

Test Targets

| Compound | Sum Affinity Score | Maximal Affinity Score | |
|---|---|---|---|
| p-Salicylic Acid | 196 | 104 | (less active) |
| m-Salicylic Acid | 219 | 98.3 | (less active) |
| Benzoic Acid | 214 | 108 | (less active) |

EXAMPLE 5

A simulated receptor with specific affinity for salicylates. This receptor was optimized first to detect benzoic acid, then o-salicylate. It is selective for the ortho isomer, but equally sensitive to the benzoic acid moieties in p- and m-Salicylic acid.

Optimized Correlation Score: 0.97

Training Targets used to optimize selective affinity. The target affinities used are fictitious.

| Compound | Target Affinity | Sum Affinity Score | Maximal Affinity Score |
|---|---|---|---|
| Benzene | 0.7 | 12.5 | 1.8 |
| Benzoic Acid | 5.9 | 71.9 | 12.5 |
| o-Salicylic Acid | 8.9 | 91 | 17.4 |

Test Targets

| Compound | Sum Affinity Score | Maximal Affinity Score |
|---|---|---|
| p-Salicylic Acid | 56.2 | 12.4 (less active) |
| m-Salicylic Acid | 40.1 | 12.9 (less active) |
| Benzoic Acid | 71.9 | 12.5 |
| o-Salicylic Acid | 91 | 17.4 |

EXAMPLE 6

Two simulated receptors with stereospecific affinity for salicylates. Receptor A is discriminates more strongly between o-salicylic acid and benzoic acid than receptor B. This difference was established by the target affinities assigned during the training process.

Optimized Correlation Score: Receptor A : 0.99; Receptor B 0.99

Training Targets used to optimize selective affinity. The target affinities used are fictitious.

| Compound | Target Affinity | Sum Affinity Score | Maximal Affinity Score |
|---|---|---|---|
| Benzene | 0.9 | 11.1 | 6.6 |
| Benzoic Acid | 2.4 | 42.9 | 13.1 |
| o-Salicylic Acid | 4.1 | 70.1 | 24.8 |

Test Targets

| Compound Sum | Affinity Score | Maximal Affinity Score |
|---|---|---|
| p-Salicylic Acid | 31.5 | 13.6 (less active) |
| m-Salicylic Acid | 36.6 | 16 (less active) |

| Compound | Target Affinity | Sum Affinity Score | Maximal Affinity Score |
|---|---|---|---|
| Benzene | 0.9 | 20 | 6.2 |
| Benzoic Acid | 2.2 | 41 | 15.5 |
| o-Salicylic Acid | 3.1 | 51 | 19.5 |

Test Targets

| Compound | Sum Affinity Score | Maximal Affinity Score |
|---|---|---|
| p-Salicylic Acid | 34 | 16 (less active) |
| m-Salicylic Acid | 52 | 22 (similar to o-salicylic acid) |

Note that Receptor B is more strongly affected by the similarities between the compounds and benzoic acid.

EXAMPLE 7

Four simulated receptors lacking specific affinity for salicylates. This was established by assigning benzoic acid and o-salicylic acid similar target affinities during the training process. As a result, all four receptors are primarily sensitive to the benzoic acid moiety of the salicylic acids and largely ignore the contribution of the hydroxyl group.

Optimized Correlation Score: Receptor A: 0.997; Receptor B: 0.97; Receptor C: 0.96; Receptor D: 0.995

Training Targets used to optimize selective affinity. The target affinities used are fictitious. Twenty-five tests per target.

Target Affinities for All Receptors

| Compound | Target Affinity |
|---|---|
| Benzene | 0.5 |
| Benzoic Acid | 4.7 |
| o-Salicylic Acid | 5.0 |

Receptor Affinities

| | Sum Score | | | | Maximal Score | | | |
|---|---|---|---|---|---|---|---|---|
| Compound | A | B | C | D | A | B | C | D |
| Benzene | 7.5 | 28.4 | 1.2 | −2.8 | 5.9 | 5.8 | 2.5 | 2.8 |
| Benzoic Acid | 54.5 | 102 | 29 | 69 | 29.6 | 19.9 | 9.3 | 25.3 |
| o-Salicylic Acid | 53.6 | 97.8 | 22.7 | 73.7 | 32.6 | 17.9 | 10.8 | 26.8 |

Test Targets

| | Sum Score | | | | Maximal Score | | | |
|---|---|---|---|---|---|---|---|---|
| Compound | A | B | C | D | A | B | C | D |
| m-Salicylic | 15.4 | 106 | 25.2 | 61.5 | 28.0 | 18.9 | 8.6 | 24.7 |
| p-Salicylic Acid | 50.4 | 104 | 18.5 | 59.5 | 28.8 | 20.1 | 9.5 | 23.4 |
| o-Salicylic Acid | 53.6 | 97.8 | 22.7 | 73.7 | 32.6 | 17.9 | 10.8 | 26.8 |

EXAMPLE 8

Three simulated receptors with specific affinity for positional isomers of chlorinated arenes. This was established by assigning chlorobenzene and o-dichlorobenzene very different target affinities during the training process.

Optimized Correlation Score: Receptor A: 0.987, Receptor B: 0.992, Receptor C: 0.996.

Training Targets used to optimize selective affinity.

The target affinities used are fictitious. Twenty-five tests per target.

Target Affinities for All Receptors

| Compound | Target Affinity |
|---|---|
| Benzene | 0.9 |
| Chlorobenzene | 2.5 |
| o-Dichlorobenzene | 5.8 |

Receptor Affinities

| | Sum Score | | | Maximal Score | | |
|---|---|---|---|---|---|---|
| Compound | A | B | C | A | B | C |
| Benzene | 39.7 | 17.1 | 31.0 | 3.7 | 3.2 | 3.4 |
| Chlorobenzene | 81.8 | 45.4 | 76.2 | 9.0 | 11.9 | 12.9 |
| o-Dichlorobenzene | 147.3 | 90.9 | 170.5 | 19.9 | 23.2 | 21.1 |

Test Targets

| | Sum Score | | | Maximal Score | | |
|---|---|---|---|---|---|---|
| Compound | A | B | C | A | B | C |
| m-Dichlorobenzene | 68.0 | 73.9 | 145.6 | 17.2 | 17.0 | 18.5 |
| p-Dichlorobenzene | 112.4 | 92.5 | 132.6 | 12.0 | 14.6 | 10.7 |
| o-Dichlorobenzene | 147.3 | 90.9 | 170.5 | 19.9 | 23.2 | 21.1 |

PART B: Development of Novel Compounds with Selected Functional Characteristics Evolution of Novel Ligands A population of simulated receptors evolved for selective affinity to a set of target compounds with similar functional characteristics can be used to devise novel compounds with similar characteristics, provided these characteristics are closely correlated with the structure or binding affinity of the model compounds. Using interaction with the receptors as selection criteria, novel chemical structures can be evolved to optimally fit the receptors. Because these compounds must meet the necessary and sufficient requirements for receptor selectivity, these novel compounds are likely to also possess activity similar to that of the original molecular targets.

Overview of Process

1. Generate a population of simulated receptors with optimized selectivity for a set of characterized target compounds. In some cases it may be desirable to generate several populations with different affinity characteristics. For example, three populations of simulated receptors could be generated, the first mimicking the properties of the selected target site, the second mimicking a site required for transport of the ligand to its primary target and a third population of simulated receptors mimicking a target site mediating undesirable side-effects. The development of a new ligand structure in this instance would require simultaneous optimization of affinity for the first two receptor populations and minimizing affinity for the third population.

2. Determine the affinity of a novel primary structure for the simulated receptor population(s).

3. Modify primary structure and evaluate affinity using simulated receptor population(s). If the modification improves affinity characteristics, the modified structure is retained for further modification. Otherwise a different modification is tested. Previously rejected modifications may be reintroduced in combination with other modifications.

4. Step 3 is repeated until a compound with suitable affinity characteristics is obtained.

Note: Using suitably discriminating simulated receptors it is possible to evolve chemical structures with sub-maximal affinity for a selected target site.

1) Molecular Genotype Code Generation

Encoding of the ligand phonotype (molecular structure) in the form of a linear genotype represented by a character string facilitates the processes of mutation, recombination and inheritance of the structural characteristics of the ligand during the evolutionary process.

The ligands evolved by the current implementation consist of substituted carbon skeletons. Each code consists of three character vectors. The primary code vector contains the turning instructions for the generation of the carbon skeleton and determines the position of each carbon atom in the skeleton. The secondary code vector identifies the functional groups attached to each carbon atom. The tertiary code vector specifies the position of the functional group relative to the host carbon. Molecular skeletons combining atoms other than carbon (e.g. ethers, amides and heterocycles) can be constructed in a homologous fashion using additional characters in the code to specify atomic species replacing carbon atoms in the skeleton.

The carbon skeleton is constructed from a series of points which form the nodes of a three-dimensional tetrahedral coordinate system. During initial skeleton construction, the distance between nearest points is equal to the mean bond length between alkyl carbon atoms.

Primary code vector: ligand skeleton determinants

The primary code vector consists of characters identifying turning direction relative to the current atom position. Each turning direction specifies the coordinates of the next atom in the tetrahedral matrix. Four directions (1,2,3,4) can be taken from each atom, corresponding to the unfilled valences of $Sp^3$ carbon. Each of the carbon atoms belongs to one of four possible states (A, B, C, D). These states correspond to the number of distinct nodes in the tetrahedral coordinate system.

The relationship between turn direction and the new coordinates for the next atom in the skeleton is given by the following tables. The two tables B1 and B2 below embody the two turning conventions required to construct the ligands. The boat convention results in the generation of a tetrahedral matrix in which closed 6-member rings (cyclohexanes) assume the boat configuration. The chair convention results in the generation of a matrix in which cyclohexyl rings assume the chair configuration. It is possible to combine both conventions during code generation. Only the boat convention is used in the examples discussed here.

TABLE B1

Boat Convention
Current Position = (x, y, z)

| | New Position Following Turn | | | |
|---|---|---|---|---|
| Current State | Turn = 1 | Turn = 2 | Turn = 3 | Turn = 4 |
| A | (x − .75, y + .433, z − .5) | (x + .75, y + .433, z − .5) | x, y − .864, z − .5) | (x, y, z + 1) |
| B | (x + .75, y − .433, z + .5) | (x − .75, y − .433, z + .5) | (x, y + .864, z + .5) | (x, y, z − 1) |
| C | (x − .75, y + .433 z + .5) | (x + .75, y + .433, z + .5) | (x, y − .864, z + .5) | (x, y, z − 1) |
| D | (x + .75, y − .433, z − .5) | z − .75, y − .433, z − .5) | (x, y + .864, z − .5) | (x, y, z + 1) |

Each turn also results in the specification of the state of the new atom:

| | New State Following Turn | | | |
|---|---|---|---|---|
| Current State | Turn = 1 | Turn = 2 | Turn = 3 | Turn = 4 |
| A | B | B | B | C |
| B | A | A | A | D |
| C | D | D | D | A |
| D | C | C | C | B |

TABLE B2

Chair Convention
Current Position = (x, y, z)

| | New Position Following Turn | | | |
|---|---|---|---|---|
| Current State | Turn = 1 | Turn = 2 | Turn = 3 | Turn = 4 |
| A | (x − .75, y + .433, z − .5) | (x + .75, y + .433, z − .5) | x, y − .864, z − .5) | (x, y, z + 1) |
| B | (x + .75, y − .433, z + .5) | (x − .75, y − .433, z + .5) | x, y + .864, z + .5) | (x, y, z − 1) |
| C | (x − .75, y − .433, z + .5) | (x + .75, y − .433, z + .5) | (x, y + .864, z + .5) | (x, y, z − 1) |
| D | (x + .75, y + .433, z − .5) | (x − .75, y + .433, z − .5) | (x, y − .864, z − .5) | (x, y, z + 1) |

Each turn also results in the specification of the state of the new atom:

| | New State Following Turn | | | |
|---|---|---|---|---|
| Current State | Turn = 1 | Turn = 2 | Turn = 3 | Turn = 4 |
| A | B | B | B | C |
| B | A | A | A | D |
| C | D | D | D | A |
| D | C | C | C | B |

Using these relationships, primary code vectors consisting of strings of the characters 1,2,3, and 4 can be decoded to create three-dimensional arrangements of carbon atoms. The resulting string of carbon atoms is allowed to fold back on itself or create closed loops, producing short side chains and ring structures. Specific ring structures (for example, cyclohexanes) can be incorporated directly as specific character sequences, as shown below.

Secondary Code Vector: Substituents

A secondary code vector, of the same length as the primary code vector, is used to allocate the type of substituent attached to the carbon atom specified by the primary code vector. Each substituent is identified by a single character. Substituents are added singly to the carbon skeleton. A single carbon atom can have more than one substituent, but only if it is specified more than once by the primary code.

In the current implementation, all valences not filled by substituents specified by the secondary code vector are automatically filled with hydrogen atoms during the ligand construction process. Other rules could be applied for filling empty valences with atoms other than hydrogen.

Tertiary Vector: Substituent Bond Vector

A tertiary code vector, of the same length as the primary code vector, is used to allocate the valence used for the attachment of the substituent specified by the secondary code vector. The tertiary code consists of the characters 1, 2, 3, and 4 each of which refers to the turn directions specified for the primary code. Substituents are only allocated if the valence is not already occupied by either a carbon atom specified by the primary code vector or another previously allocated substituent. Alternatively, successive substituents could replace previously allocated substituents.

2) Code Creation

To create carbon skeletons the primary code is constructed by creating a random sequence of characters belonging to the set {"1", "2", "3", "4"}. The creation of heterocyclic structures, ethers, amides, imides and carboxylic compounds is accomplished by substituting a carbon atom in the skeleton by a different atom specified by the secondary code.

The secondary code is generated from a random sequence of characters identifying substituent types. The frequency of the characters can be random or fixed prior to code generation.

The tertiary code consists of characters belonging to the set {"1", "2", "3", "4"}. Ring structures can be deliberately constructed (as opposed to random generation) by adding specific character sequences to the primary code. For example "1431413" codes for a cyclohexyl ring. A total of 24 strings code for all possible orientations of cyclohexyl rings in the tetrahedral matrix. Secondary and tertiary code vectors for the ring primary codes are generated as described previously. Module 12 provides a flowchart of an example creation of code generating carbon skeletons with rings.

The relative positions of the entry and exit points from a ring comprising part of the carbon atom skeleton are determined by the length of the character sequences used to generate the ring. Specifically, if the sequences contains six characters, for example 431413, then the entry and exit point will be the same member of the ring. If the sequence is partially repeated and appended to the initial six characters, the entry point and exit point will not be the same member of the ring. For example, the sequences 4314134 and 43141343141 will generate rings with exit points at the members of the rings adjacent to the entry points.

In the current implementation, rings are added to the skeleton by adding sequences of 6 or more characters to the code. For the ring defined by 431413 the possible sequences used are:

431413
4314134
43141343
431413431
4314134314
43141343141
431413431413
431413431413

The conventions presented for creating a novel ligand genotype can be used to encode other chemical structures in a linear format, either for storage or for introduction into the ligand evolutionary process. For example, a known pharmacophore can be encoded in linear format and used as the starting point for evolving novel ligands with similar or enhanced functional properties. Similarly, sets of pharmacophores interacting with a common target site can be encoded in linear format and used for recombination.

3) Code Translation and Ligand Construction

The code vectors are converted into three-dimensional representations of ligands in a translation process consisting of three discrete steps. In the first step, the carbon atom skeleton is constructed using the primary code. In the second step substituents are added to the carbon skeleton using the instructions from the secondary and tertiary code vectors. Instructions from the secondary and tertiary code vectors may also specify replacement of carbon atoms in the skeleton with different atoms. Instructions from the secondary and tertiary codes may also change the number and orientation of available valences present on a carbon or other atom forming part of the primary skeleton. For example, addition of carbonyl oxygen occupies two empty valences. In the third step, all valences not filled by substituents during the second step are filled with hydrogen atoms (unless otherwise specified).

Primary Decoding: Ligand Skeleton Construction

Primary decoding uses the turning instructions from the primary code vector to specify the positions of each carbon atom. The first atom is assumed to be located at the origin of the coordinate system. The first atom is assumed to occupy state A in the matrix.

Decoding proceeds sequentially. The result of the primary decoding process is a 3×n matrix containing the x, y, and z coordinates of each of the n carbon atoms in the skeleton. Because loops and reversals are permitted, the same position in space may be occupied by more than one carbon. In these cases, only one carbon atom is assumed to occupy the position. As a result, the number of carbon atoms forming the completed skeleton may be less than the number of characters in the primary code vector.

As the primary code is read, a list is constructed from the secondary code that identifies the substituents attached to each carbon position. At the same time a parallel list is constructed using the tertiary code to specify the valence occupied by each substituent.

Secondary Decoding: Substituent Additions

Substituents are added sequentially to each carbon atom based on the list generated from the secondary code during primary decoding. The corresponding value from the tertiary code is used to specify the valence position of the substituent relative to the host carbon. If the position is already occupied by either an adjacent carbon atom, or a previously specified substituent, the substitution is not carried out. Alternatively, a decoding process could be constructed in which the substitution is carried out at the next unoccupied position or the substitution replaces a previously specified substituent. The distance between the substituent and the carbon atom is calculated from look up tables of bond lengths. The position data and bond lengths are used to calculate the coordinates of the substituent. In the case of multi-component substituents, such as hydroxyl, nitro, and amino groups, the coordinates for each atom in the substituent are calculated relative to the host carbon.

After all the substituents specified by the secondary code vector are added to the skeleton, all unfilled positions remaining on the skeleton are filled with hydrogen atoms. The hydrogen $sp^3$-carbon bond length is used to calculate the coordinates of each hydrogen atom.

A single carbon atom can have more than one non-hydrogen substituent. This can occur if the same position is specified more than once by the primary code vector. The current implementation does not incorporate multiple substitutions using the secondary code directly, although this can be readily implemented.

Substitutions are only allowed at loci not occupied by carbon atoms forming the ligand skeleton. A cumulative list is maintained of all occupied sites in the tetrahedral matrix.

During the secondary decoding process a list is compiled of the type, radius, and position of all the atoms comprising the ligand. This list is the basis for subsequent target generation.

At this stage in the process, the feasibility of the structure generated from the code sequence is not evaluated. In some cases the atomic coordinates may be entered into energy minimization programs to create more realistic structures. However, in the present implementation, no assumptions are made concerning the configuration of the ligand during binding. In addition, the current implementation preserves the structural uniqueness of specific configurations of the same molecule. For example, the current implementation distinguishes between three rotational isomers of butane, and treats each isomer as a unique molecule.

The code vectors constitute the genotype of the corresponding ligand, and can be subjected to mutation and recombination with resulting changes in ligand structure. The ligand structure itself is the phenotype used to evaluate binding affinity with a selected population of virtual receptors.

4) Target Presentation

Chemical structures or target ligands are initially constructed from randomly generated codes. Following decoding, the coordinates, radii, dipole moments and polarizabilities of each atom in the target ligand are obtained from look up tables of value and used to evaluate the binding affinity between the ligand and a selected population of virtual receptors.

The affinity of the target for each of the virtual receptors is tested for many orientations of the target relative to the receptor surfaces. No assumptions are made concerning the relative orientations of the ligand and simulated receptor. Prior to the evaluation of binding affinity, the target and receptor must be brought into contact. The method of target presentation and calculation of affinity between the chemical structures and simulated receptors is essentially the same as discussed above in Module 4 between known target molecules and the simulated receptors.

5) Evaluation of Binding Affinity and Fitness

The binding affinity of the target ligand for each of the simulated receptors used for fitness evaluation is calculated using the same effective affinity calculation method described for simulated receptor generation using the target molecules. As previously noted, affinity calculations using other criteria can be incorporated into the fitness testing process but the efficacy and computational efficiency of the present invention relies in part on using the same effective affinity calculation for virtual receptor generation and generation of the chemical structures using the simulated receptor populations.

6) Ligand Evolution

Testing Goodness of Fit

Goodness of fit between a selected population of simulated receptors and a novel ligand or chemical structure is evaluated by comparing the target activity or affinity values for the ligand with those obtained for the simulated receptor-ligand complexes. The maximal affinities of an optimally selective virtual receptor should be strongly correlated with the target affinity measures. Successive iterations of the evolutionary process are used to enhance this correlation.

The target values can be set to any level of binding affinity. It is not required that the ligand have the same binding affinity for all the virtual receptors used in the selection process. In the current implementation, the maximal binding affinities of the optimized virtual receptors for known substrates are used to calculate target binding affinities. For example, the target affinities may be set to 90% of the binding affinity of each member of the virtual receptor population for a specific substrate. Alternatively, the target binding affinity may be set to zero if the interaction between the ligand and the virtual receptor is to be minimized.

By combining simulated receptors optimized for different sets of substrates and associating selected target affinity values with each receptor, novel ligands can be selected for specific binding affinity profiles. Ligand fitness measures the match between calculated ligand binding affinities and the target affinity values. The optimization process maximizes ligand fitness.

The optimal orientation of the ligands for maximal binding affinity is unknown prior to testing. In order to obtain a representative measure of the range of receptor-ligand affinities, each novel ligand must be tested repeatedly using different random orientations relative to the receptor surface. Each test uses Module 4 discussed in Part A to evaluate affinity. In general, the reliability of the maximal affinity values obtained depends upon the sample size, since it becomes increasingly likely that the sample will contain the true maximal value.

Two techniques are employed in the current implementation to circumvent the need for large sample sets for the generation of optimized novel ligands or chemical structures:

1. The use of a measure combining average (or sum) affinity and maximal affinity to select for ligands with optimized affinity profiles.

2. Incremental increases in the number of orientations tested with successive iterations of the optimization process. (Optimization begins with a small set of target orientations, as ligands of greater fitness are generated, more orientations are tested.)

In the current implementation, the sum is calculated for the affinity values obtained for all the tested orientations of each ligand. This sum affinity score is a measure of the average affinity between the receptor and the ligand. At the same time, the maximal affinity value is also determined.

Both sum and maximal affinities are used to test the goodness of fit between the virtual receptor and the novel ligand. The fitness of each novel ligand is rated according to the difference between the calculated values of sum affinity and maximal affinity and the target values for these parameters. In the current implementation, the value:

$$F = \left\{ \frac{|\text{calculated max affinity} - \text{target max affinity}|}{2 \times \text{target max affinity}} \right\} + \left\{ \frac{|\text{calculated sum affinity} - \text{target sum affinity}|}{2 \times \text{target sum affinity}} \right\}$$

is calculated as the fitness score for each novel ligand-simulated receptor pair. FITNESS IS MAXIMAL WHEN THE FITNESS SCORE IS ZERO. Target maximal affinity and target sum affinities are obtained from the regression functions developed during the evolution of optimized virtual receptors, as described in the previous sections. The target values are obtained as follows:

target max affinity=f×maximal affinity of the most potent substrate used for virtual receptor generation target sum affinity=f×sum affinity of the most potent substrate used for virtual receptor generation where f=a scaling factor.

When more than one simulated receptor is used for the evaluation of ligand fitness, the fitness scores of each ligand-simulated receptor pair are summed.

$$F_{tot} = \sum_{i=1}^{n} F_i$$

$$F_i = \left\{ \frac{|\text{calculated max affinity}_i - \text{target max affinity}_i|}{2 \times \text{target max affinity}_i} \right\}$$
$$\left\{ \frac{|\text{calculated sum affinity}_i - \text{target sum affinity}_i|}{2 \times \text{target sum affinity}_i} \right\}$$

In this case, fitness is maximized when the sum of the fitness scores is zero. In some cases it may be desirable to use only the maximal affinity scores when testing a novel ligand against a panel of different simulated receptors. In this case the fitness would be given by:

$$F_{tot} = \sum_{i=1}^{n} |\text{calculated max affinity}_i - \text{target max affinity}_i| / \text{target max affinity}_i.$$

In this case, fitness is also maximized when the sum of the fitness scores is zero. Other methods, for example the use of a geometric mean, could also be used to measure the total fitness of a ligand tested against a series of simulated receptors.

Use of both the maximal affinity values and sum affinity values obtained for each simulated receptor ensures that the selectivity of the virtual receptors is implicated in the evaluation of ligand fitness. In this way, the fitness of the ligand reflects not only the affinity of the ligand but also satisfaction of the steric requirements of the virtual receptor that are the basis of selectivity.

6a) The Optimization Process

Objective

To evolve a novel ligand that has selected target affinities for a set of simulated receptors. A highly efficient mechanism for finding solutions is required, since the total number of possible genotypes containing 25 instructions is $256^{25}$.

Process (1) PHASE 1. Generate a set of random genotypes coding for ligands and screen against a set of simulated receptors to select ligands exceeding a threshold level of fitness.

(2) PHASE 2. The selected genotype is used as the basis for further optimization using genetic algorithm (recombination) and unidirectional mutation techniques. Mutate selected genotype to generate a breeding population of distinct but related genotypes for recombination.

(3) Choose most selective mutants from population from population for recombination.

(4) PHASE 3. Generate new genotypes by recombination of selective mutants. Select from the resulting genotypes those with the highest affinity fitness. Use this subpopulation for the next recombinant (repeat PHASE 3) or mutation (repeat PHASE 4) generation.

(5) PHASE 4. Take best recombination products and apply repeated point mutations to enhance selectivity.

(6) The optimization process is completed when ligands of desired fitness are generated.

PHASE I: Evolution-Generation of Primary Code

The objective of the first stage in the optimization process is to generate a genotype and corresponding ligand phenotype with a minimal level of fitness. This genotype is subsequently used to generate a population of related genotypes.

The Genetic Algorithm developed by Holland can be used to search for optimal solutions to a variety of problems. Normally this technique is applied using large, initially random sets of solutions. In the present implementation the technique is significantly modified in order to reduce the number of tests and iterations required to find ligands with high selective affinity. This has been accomplished by using a set of closely related genotypes as the initial population and the application of high rates of mutation at each iteration. For any set of target compounds it is possible to develop distinct ligands with optimal affinity characteristics. For example, receptors may bind optimally to the same targets but in different orientations. The use of an initial population of closely related genotypes increases the likelihood that the optimization process is converging on a single solution. Recombination of unrelated genotypes, although it may generate novel genotypes of increased fitness, is more likely to result in divergence.

PHASE 2: Ligand Mutation

The objective of the second phase of the evolutionary process is the generation of a population of distinct but related genotypes derived from the primary genotype. Members of this population are subsequently used to generate recombinants. This breeding population is created by multiple mutation of the primary genotype. The resulting genotypes are translated and screened for selectivity. The most selective products are retained for recombination.

Ligands are subjected to mutation by changing characters in the genotypes (code vectors) encoding their structures. These mutations change the shape of the ligand, as well as functional group placement and functional group types present on the ligand. Mutations in the current implementation can alter the number of carbons comprising the ligand skeleton. Module 12 is a flowchart of a sample process for multiple point mutation.

Mutations can alter the folding pattern of the ligand phenotype, with resulting changes in shape and the location or exposure of functional groups. Mutations that affect the configuration of peripheral regions of the ligand phenotype can result in shifts in position relative to the receptor center.

Neutral Mutations

All mutations alter the structure of the phenotype, however, not all mutations result in changes in the functionality of the ligand. Such neutral mutations may alter components of the ligand that do not affect affinity. In some cases these neutral mutations can combine with subsequent mutations to exert a synergistic affect.

Sequence Mutations

Sequence mutations do not change code characters directly. Instead the sequence of characters in the code is rearranged. Sequence mutations can alter the size of the ligand, the structural configuration and presence and location of functional groups. Four types of sequence mutation are used in the current implementation:

a) DELETION: A sequence of characters is removed from the code.

ABCDEA→ABEA b) INVERSION: The order of characters comprising a sequence within the code is reversed.

ABCDEA→ABDCEA c) DUPLICATION: A sequence of characters comprising part of the code is repeated.

ABCDEA→ABCDCDEA d) INSERTION: A sequence of characters is inserted into the code.

ABCDEA→ABCDBCEA

Mutations are applied in combination in the current implementation. Module 13 provides a flowchart of a sample sequence mutation.

PHASE 3: Generation of Recombinant Code

During recombination, randomly chosen, complementary sections are exchanged between selected genotypes. The objective of recombination is the generation of novel genotypes with increased fitness. Recombination facilitates the conservation of genotype fragments that are essential for phenotypic fitness, while at the same time introducing novel combinations of instructions. In general, recombination coupled with selection results in rapid optimization of selectivity. Module 14 provides a flowchart for a sample procedure for recombination.

The current implementation retains the population used for recombination for testing. This ensures that genotypes with high selectivity are not replaced by genotypes with lower fitness. In the current implementation, multiple mutations are applied to 50% of the recombinant genotypes prior to testing. This process increases the variability within the recombinant population. The test populations used in the current implementation range in size from 10 to 40 genotypes. This is a relatively small population size. Under some conditions, larger populations may be required. Module 14 is a flowchart for an example of recombination.

PHASE 4: Ligand Maturation

Progressive Micromutation Technique

The final stage in the optimization process mimics the maturation of antibodies in the mammalian immune system. A series of single point mutations are applied to the genotype, and the effect on phenotypic fitness is evaluated. Unlike recombination, this process generally results in only small incremental changes to the selectivity of the phenotype. The maturation process uses a Rechenberg (1+1) evolutionary strategy. At each generation the fitness of the parental genotype is compared to that of its mutation product, and the genotype with the greater selectivity is retained for the next generation. As a result, this process is strictly unidirectional, since less selective mutants do not replace their parents. During each iteration of the maturation process, only a single instruction in the code is changed in the present implementation.

If a parent and its mutation product have the same selectivity, the parent is replaced by its product in the next generation. This method results in the accumulation of neutral mutations that may have synergistic effects with subsequent mutations. This convention is arbitrary. Module 15 provides a flowchart for a sample maturation process.

If recombination or maturation do not generate improved selectivity after repeated iterations, it may be necessary to repeat multiple mutations (PHASE 2) in order to increase the variability of the breeding population genome.

Examples of Ligand Generation

Overview

The mosquito *Aedes aegypti* is repelled by benzaldehyde and, to a much smaller degree, by benzene and toluene (Table 1). This species is not repelled significantly by cyclohexane or hexane (Table 1). In the following test of novel ligand generation, the method is used to generate, ab initio, compounds that will be similar in repellent activity to benzaldehyde. In the first step of ligand generation, simulated receptors were constructed with high affinity for benzaldehyde and low affinity for benzene. In the second step, ligands are evolved with binding affinities for the simulated receptors similar to that of benzaldehyde.

Mosquito Responses

Mosquitoes were lab-reared, 7–14 days post-emergence and unfed. Experiments were conducted over six day periods at 20° C. under fluorescent lighting. Tests were run between 12:00 and 17:00 EDT. The test populations in the four sets of trials consisted of 200, 175, 105 and 95 females. Mosquitoes were provided with drinking water.

The tests were conducted in a 35×35×35 cm clear Plexiglas box with two screened sides forming opposite walls. The screening consisted of two layers: an inner layer of coarse plastic mesh and an outer layer of fine nylon mesh. The box was placed in a fumehood such that air entered one of the screened sides and exited through the opposite side. Air flow was <0.5 cm/s.

The mosquitoes landed on the walls of the box, oriented head upwards. Triangular pieces (4×4×1 mm) of Whatman #1 filter paper were used to present the stimulant compounds. The tips were dipped into the test solution to a depth of 0.5 cm and used immediately. Responses to the test solutions were determined as follows:

1. A stationary female resting on the interior screen of the upwind wall was selected for testing.
2. The treated filter paper tip was placed against the outside of the screen and positioned opposite the mesothoracic tarsus of the mosquito. In all cases the initial approach was made from below the position of the mosquito.
3. The tip was held in position for a maximum of 3 s and the response of the mosquito was noted.

The procedure was then repeated for a new individual. Mosquitoes were tested only once each day with each compound. Tips were used for five tests each (total duration of use <30 s), then replaced. Compounds were tested in random order, and each compound was tested twice on separate days. Two sets of controls were conducted using untreated (dry) filter paper tips and tips moistened with distilled water positioned in the same manner as treated tips. Tests of these controls were interspersed regularly among tests of the repellent compounds. Responses to the controls did not vary during the course of the experiment (p>0.25).

Four behavioral responses were recorded:

1. No response: the mosquito remained motionless.
2. Take-off: the mosquito flew away from its resting site.
3. Ipsilateral leg lifting: the mosquito raised the mesothoracic leg on the same side as the stimulus source.
4. Contralateral leg lifting: the mosquito raised the mesothoracic leg on the opposite side from the stimulus source.

Ipsilateral leg lifting was frequently followed by take-off, in which case both behaviors were recorded. Polyethylene gloves were worn during testing an during all phases of compound preparation.

TABLE E1

Mosquito responses to selected volatile compounds

| Compound | Boiling Point (° C.) | N | % Flight Response | % Leg Lifting Response | Relative Repellency* |
|---|---|---|---|---|---|
| Benzaldehyde | 178 | 130 | 90 | 10 | 178 |
| Benzene | 80 | 72 | 72 | 12.5 | 68 |
| Toluene | 110 | 166 | 67 | 27 | 94 |
| Cyclohexane | 81 | 80 | 6 | 0 | 4.9 |
| Hexane | 69 | 100 | 4 | 0 | 2.8 |
| Control (blank) | — | 450 | 5 | 0 | |

*Relative repellency = [(%Flight Response + % Leg Response) × Boiling Point]/ 100

Simulated Receptor and Ligand Generation

Two simulated receptors were generated using the same selection criteria. Each receptor was used independently to generate a set of ligands.

Molecular Assembly 1

PHASE 1: RECEPTOR GENERATION

A receptor was evolved with selective affinity for benzaldehyde.

The training targets were benzene and benzaldehyde. Fifteen orientations of each target were used to calculate affinity values.

Results of the evolutionary process were:

| Target | Activity Level | Sum Affinity | Maximum Affinity |
|---|---|---|---|
| Benzene | 1.0 | 6.87 | 2.21 |
| Benzaldehyde | 5.9 | 75.87 | 13.02 |

The affinity score for the receptor was 0.992 Code for the Optimized 25×6×7 Benzaldehyde Receptor:

| | | | |
|---|---|---|---|
| 231014406145 | 053400324221 | 412100131300 | 063112101132 |
| 412061421302 | 413231124335 | 133100333032 | 300043541401 |
| 022224-31514 | 143431012321 | 341310334122 | 101414141021 |
| 402131114311 | 010233120331 | 260214016231 | |

Phase 2: Ligand Generation

The optimized simulated receptor was used as a template for the evolution of novel ligands. Four different ligands were assembled by random mutation and selection. Ligands were selected for similarity with benzaldehyde. The affinity values for the ligands were:

|  | Benzaldehyde | Ligand 1.1 $C_9H_{17}C_{12}OH$ | Ligand 1.2 $C_8H_{15}Cl$ | Ligand 1.3 $C_8H_{13}Cl$ (=0) | Ligand 1.4 $C_{13}H_{16}OH$ (=0) |
|---|---|---|---|---|---|
| Sum Affinity | 75.87 | 74.03 | 67.88 | 72.25 | 72.94 |
| Max. Affinity | 13.02 | 12.82 | 15.14 | 12.58 | 11.2 |

Figure 4A:
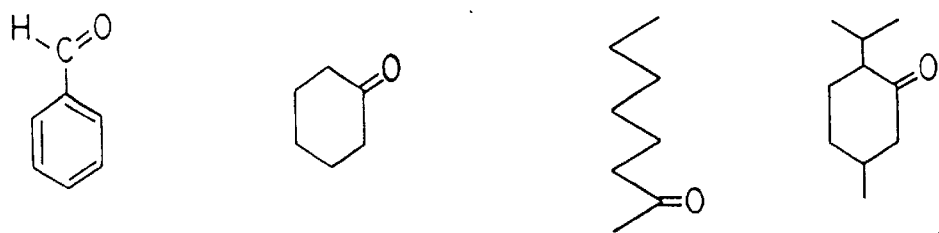
FIG. 4a shows several chemical compounds used in the example relating to examples of ligand generation.
Figure 4B:
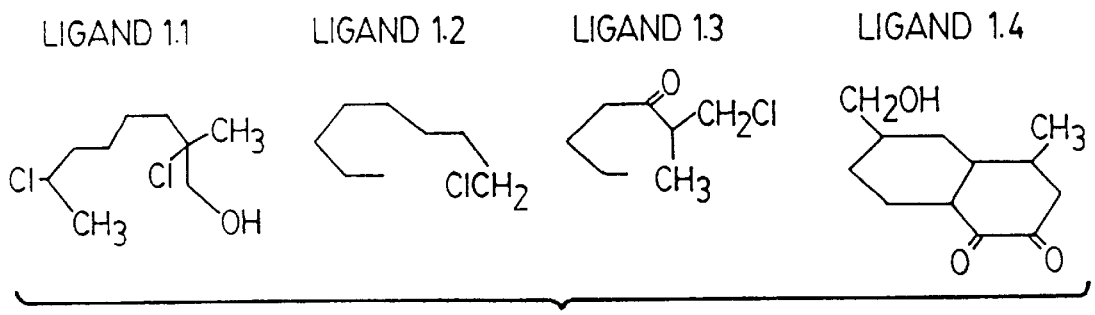
FIG. 4b shows ligands 1.1 to 1.4 generated by the method of the present invention in the example of ligand generation wherein each ligand has at least one orientation wherein it is structurally similar to benzaldehyde.

Evolved ligands 1.1 to 1.4 are shown in FIG. 4b. At least one orientation of each ligand was structurally similar to benzaldehyde.

Molecular Assembly 2

Phase 1: Receptor Generation

A 25×6×7 receptor was evolved with selective affinity for benzaldehyde. The training targets were benzene and benzaldehyde. Fifteen orientations of each target were used to calculate affinity values.

Results of the evolutionary process were:

| Target | Activity Level | Sum Affinity | Maximum Affinity |
|---|---|---|---|
| Benzene | 1.0 | 25.88 | 8.53 |
| Benzaldehyde | 5.8 | 162.23 | 42.74 |

The affinity score for the receptor was 0.996

The code for the receptor was:

```
0312644413 13   004422243042   223140112054   302122330134
543301114446    210043042311   323431131340   130020120133
224223503403    432003432122   002221221113   411440003113
323030313214    002321144010   000243013133
```

Phase 2: Ligand Generation

The optimized simulated receptor was used as a template for the evolution of novel ligands. Four different ligands were assembled by random mutation and selection. Ligands were selected for similarity with benzaldehyde. The affinity values for the ligands were:

|  | Benzaldehyde | Ligand 2.1 $C_8H_{13}Cl$ (=0) | Ligand 2.2 $C_9H_{15}Cl$ (=0) | Ligand 2.3 $C_6H_{10}CN$ (=0) | Ligand 2.4 $C_9H_{13}$ (=0)$_2$ |
|---|---|---|---|---|---|
| Sum Affinity | 162.23 | 182.4 | 166.5 | 159.7 | 156.8 |
| Max. Affinity | 42.74 | 48.97 | 43.0 | 39.0 | 46.5 |
| Fitness Score |  | 0.135 | 0.02 | 0.05 | 0.06 |

Figure 4C:
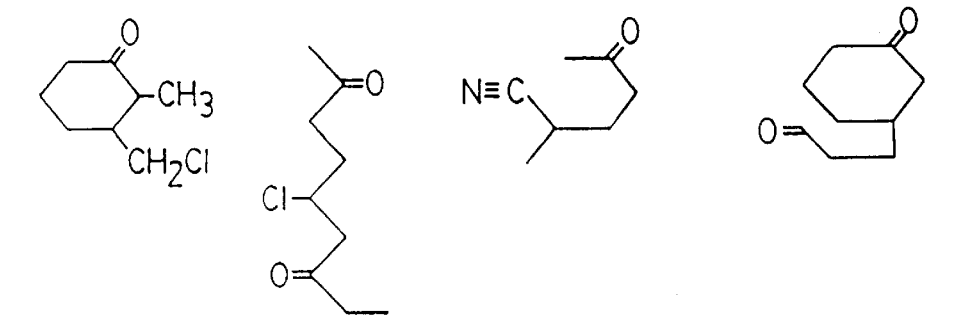
FIG. 4c shows ligands 2.1 to 2.4 generated by the method of the present invention in the example of ligand generation relating to design of chemical structural exhibiting an efficacy for repelling mosquitoes.

Evolved ligands 2.1 to 2.4 are shown in FIG. 4c. At least one orientation of each ligand was structurally similar to benzaldehyde.

Compounds 2.1 and 2.4 are substituted cyclohexanone derivatives. Ligand 2.2 is 5-Chloro-2, 7-nonadione and ligand 2.3 is 2-cyano-5-hexanone. Ligand 1.4 contains a fragment corresponding in structure to methyl cyclohexyl ketone. Experiments testing the repellency of cyclohexanone, menthone, methyl cyclohexyl ketone and 2-octanone (see FIG. 4a) suggest that these ligands will also be repellent to mosquitoes (Table E2).

TABLE E2

Mosquito responses to selected volatile compounds

| Compound | Boiling Point (° C.) | N | % Flight Response | % Leg Lifting Response | Relative Repellency* |
|---|---|---|---|---|---|
| Benzaldehyde | 178 | 130 | 90 | 10 | 178 |
| 2-Octanone | 173 | 80 | 82 | 12.5 | 162 |
| 2-Acetylcyclohexanone | 225 | 100 | 54 | 24 | 175 |
| Cyclohexanone | 156 | 134 | 99 | 1 | >=154 |
| Menthone | 207 | 110 | 72 | 11 | 172 |
| Control (blank) | — | 450 | 5 | 0 |  |

*Relative repellency = [(% Flight Response+% Leg Response) × Boiling Point] / 100

The method disclosed herein of designing new chemical structures exhibiting preselected functional characteristics or properties has been described by example only. For example, the method may be readily practice using other known or acceptable values for polarizabilities, dipole moments, covalent radii and the like. In addition, the flowcharts giving process calculation steps in the modules are meant to be illustrative only. For example, the calculation of affinity may be carried out using available computational packages using fewer approximations than used herein. The method of generating new chemical structures has relied upon first generating one or more simulated receptors exhibiting a preselected affinity for known target compounds with similar functional characteristics and using these receptors to generate the novel structures exhibiting these characteristics to whatever degree is desired. The receptors themselves may be used for other applications besides generating novel chemical structures, for example as a means of screening for pharmaceutical or toxicological properties of known compounds. Thus, it will be appreciated by those skilled in the art that numerous variations of the method disclosed herein may be made without departing from the scope of the invention.

TABLE 1

Transition states and addition factors

| Old State | Addition factors | | | New State for Turn = | | | |
|---|---|---|---|---|---|---|---|
|  | Δx | Δy | Δz | Right | Up | Left | Down |
| 1 | 0 | 1 | 0 | 2 | 4 | 3 | 5 |
| 2 | −1 | 0 | 0 | 15 | 6 | 1 | 24 |
| 3 | 1 | 0 | 0 | 1 | 7 | 15 | 22 |
| 4 | 0 | 0 | −1 | 12 | 23 | 14 | 1 |
| 5 | 0 | 0 | 1 | 9 | 1 | 16 | 23 |
| 6 | 0 | 0 | −1 | 11 | 20 | 10 | 2 |
| 7 | 0 | 0 | −1 | 13 | 21 | 8 | 3 |
| 8 | 0 | −1 | 0 | 7 | 9 | 24 | 14 |
| 9 | −1 | 0 | 0 | 17 | 10 | 5 | 8 |
| 10 | 0 | 1 | 0 | 6 | 14 | 22 | 9 |
| 11 | 0 | −1 | 0 | 22 | 16 | 6 | 12 |
| 12 | −1 | 0 | 0 | 18 | 11 | 4 | 13 |
| 13 | 0 | 1 | 0 | 24 | 12 | 7 | 16 |
| 14 | 1 | 0 | 0 | 4 | 8 | 18 | 10 |

TABLE 1-continued

Transition states and addition factors

| Old State | Addition factors | | | New State for Turn = | | | |
|---|---|---|---|---|---|---|---|
| | $\Delta x$ | $\Delta y$ | $\Delta z$ | Right | Up | Left | Down |
| 15 | 0 | −1 | 0 | 4 | 17 | 2 | 18 |
| 16 | 1 | 0 | 0 | 5 | 13 | 17 | 11 |
| 17 | 0 | 0 | −1 | 16 | 19 | 9 | 15 |
| 18 | 0 | 0 | 1 | 14 | 15 | 12 | 19 |
| 19 | 0 | 1 | 0 | 20 | 18 | 21 | 17 |
| 20 | 1 | 0 | 0 | 23 | 24 | 19 | 6 |
| 21 | −1 | 0 | 0 | 19 | 22 | 23 | 7 |
| 22 | 0 | 0 | 1 | 10 | 3 | 11 | 21 |
| 23 | 0 | −1 | 0 | 21 | 5 | 20 | 4 |
| 24 | 0 | 0 | 1 | 8 | 2 | 13 | 20 |

Formula for algorithm: Input (old state, turn) ⇒ output ($\Delta x$, $\Delta y$, $\Delta z$, new state)
Example: Initial position (12, 34, −18); Input: old state = 10, turn = right: Output: new state = 6, $\Delta x$ = 0, $\Delta y$ = 1, $\Delta z$ = 0; Subsequent position (12, 35, −18)

TABLE 2

Van der Waals Radii

| Element | H | F | O | N | C | Cl | S | Br | P | I |
|---|---|---|---|---|---|---|---|---|---|---|
| Van der Waals Radius (pm) | 110 | 140 | 150 | 150 | 170 | 180 | 180 | 190 | 190 | 200 |
| Relative Radius (H = 0.5) | 0.5 | 0.64 | 0.68 | 0.68 | 0.77 | 0.82 | 0.82 | 0.86 | 0.86 | 0.91 |

Based on: N. S. Issacs, 1987. Physical Organic Chemistry. Longman Scientific and Technical, New York. 828 pp.

TABLE 3

Covalent Bond Radii (pm)

| Bond Order | H | B | C | N | O | F | Si | P | S | Cl | Br |
|---|---|---|---|---|---|---|---|---|---|---|---|
| First | 28 | 88 | 77 | 70 | 66 | 64 | 117 | 110 | 104 | 99 | 114 |
| Second | | | 66.5 | 60 | 55 | | | | | | |
| Third | | | 60.2 | 55 | | | | | | | |
| Aromatic | | | 70 | | | | | | | | |

Based on values in N. S. Issacs (1987).

TABLE 4

Sample effective dipole values used for charge site assignments.

| Bond | Atom | Dipole Value (Debye) |
|---|---|---|
| C—H | H | +0.35 or +0.084* |
| | C | no charge assigned |
| ArC—H | H | +0.6 |
| | C | −0.366 or no charge assigned |
| =C—H | H | +0.336 |
| | C | −0.6 or no charge assigned* |
| C=O | O | −2.7 |
| | C | no charge assigned* or +1.35 |
| C—O—C | O | −0.8 |
| C—OH | H | +1.5 or +1.7 |
| | O | −1.1 |
| C—NH$_2$ | H | +1.3 |
| | N | −1.3 |
| C—NO$_2$ | O | −2.0 |
| | N | +4.0 |
| C≡N | N | −3.7 |
| | C | no charge assigned |
| C—S—C +1.5* | S | in thiophene or dimethyl sulphide (may be negatively charged in contexts) |
| C—N=C +1.3 | N | in pyridine or CH$_3$—N=CH$_2$  +1.5 or |
| Ar—F or C=C—F | F | −1.3 |
| C—F | F | −1.8 |
| Ar—Cl or C=C—Cl | C | −1.7 |
| C—Cl | Cl | −2.1 |
| Ar—Br or C=C—Br | Br | −1.7 |
| C—Br | Br | −2.0 |
| C—I | I | −2.0 |

*Preferred under most conditions
Each target atom is described fully by a set of eight values {$x_i$, $y_i$, $z_i$, $r_i$, $br_i$, $cr_i$, $d_i$, $\alpha_i$} where $x_i$, $y_i$ and $z_i$ are the positional coordinates relative to the geometric center of the molecule, $r_i$ = the van der Waals radius, $br_i$ = the bond or covalent radius, $cr_i$ = the collision radius (=$r_i$+0.5), $\alpha_i$ = the polarizability, and $d_i$ = the effective dipole moment value.

TABLE 5

Selected Relative Effective Polarizabilities For Selected Target Atoms

| Atom | Context | Relative Polarizability ($\alpha_i$) |
|---|---|---|
| H | C—H | 1.0 |
| H | N—H | 1.1 |
| H | O—H | 1.1 |
| H | S—H | 3.0* |
| F | C—F | 1.5* |
| Cl | C—Cl | 4.0 |
| Br | C—Br | 5.8 |
| I | C—I | 8.9* |

TABLE 5-continued

Selected Relative Effective Polarizabilities For Selected Target Atoms

| Atom | Context | Relative Polarizability ($\alpha_i$) |
|---|---|---|
| C | C—CH$_3$ | 3.7 |
| C | C—CH$_2$—C | 3.5 |
| C | C—CC$_2$—H | 3.2 |
| C | C=CH$_2$ | 4.5 |
| C | C=CH—C | 4.3 |
| C | C=CC$_2$ | 4.0 |
| C | C≡C—H | 4.9* |
| C | C≡C—C | 4.6* |
| C | Arene ring | 4.3* or 2.6 (based on benzene (delocalized electron cloud)) |
| C | C—C≡N | 4.0 |
| C | C$_3$—C—O— | 3.6 |
| C | C$_2$H—C—O— | 3.8 |
| C | CH$_2$—C—O— | 4.1 |
| C | H$_3$—C—O— | 4.4 |
| C | C$_2$—C=O | 3.6 |
| C | CH—C=O | 3.8 |
| C | C$_2$—C=N | ? |
| C | CH—C=N | ? |
| C | C$_3$—C—N | 3.1 |
| C | C$_2$H—C—N | 3.3 |
| C | CH$_2$—C—N | 3.6 |
| C | H$_3$—C—N | 3.8 |
| O | C—O—H | 2.1 |
| O | C=O | 2.1 |
| O | C—O—C | 1.8 |
| O | NO$_2$ | 1.9* |
| N | C—NH$_2$ | 3.1 |
| N | C—NH—C | 2.8* |
| N | C—NC$_2$ | 2.5* |
| N | C—NO$_2$ | 4.6* (may be larger in small molecules) |
| N | C≡N | 3.2 |
| S | C=S | 7.7 |
| S | C—S—C | ? |
| S | C—S—H | 5.0 |

*By calculation from molecular polarizabilities.
? Values can be determined from appropriate molecular data.

Module 1: Code Generation for Simulated Receptors

Step 1 Input code generation parameters: i) code length; and ii) instruction frequency.

Step 2 Initialize empty character string to store code.

Step 3 Generate random number.

Step 4 Based on random number and instruction frequency, select a character {"0", "1", . . . , "6"} to concatenate to code string. Repeat Step 4 until string length equals preset code length.

Step 5 Output code.

Module 2: Code Translation for Simulated Receptors

Step 1 Input origin coordinates for polymers comprising receptor.

Step 2 Input code for polymer.

Step 3 Read first character from code.

Step 4 If character is a turning instruction, use translation algorithm to determine subunit coordinates otherwise step 7.

Step 5 Store subunit coordinates. Assign a charge value of 0 to subunit

Step 6 If character is not the last character in code, repeat step 3 otherwise step.

Step 7 If character is a charge instruction, use translation algorithm to determine subunit coordinates assuming no turn.

Step 8 Store subunit coordinates. Assign charge value of +1 or −1 to subunit based on character.

Step 9 If character is not the last character in code, repeat step 3 otherwise step.

Step 10 Repeat steps 2 to 9 for each of the polymers comprising the receptor.

Step 11 Output coordinates and charge values of subunits.

Module 4: Target Presentation

Step 1 Input coordinates and radii of target atoms ($xt_i$, $yt_i$, $zt_i$, $radius_i$) (i=number of atoms in target) Input coordinates of receptor ($xr_j$, $yr_j$, $zr_j$, $charge_j$) (j=number of subunits in receptor)

Step 2 Generate random angular ($\Delta\theta, \Delta\phi$) and translation values ($k_x$, $k_y$).

Step 3 Rotate and translate atomic coordinates by random amounts.

Step 3a Convert target coordinates to polar form ($xt_i$, $yt_i$, $zt_i$, $radius_i$)→($\theta_i, \phi_i, \rho_i, radius_i$)

Step 3b Add random changes to angles ($\theta_i, \phi_i, \rho_i, radius_i$) →($\theta_i+\Delta\theta, \phi_i+\Delta\phi, \rho_i, radius_i$)

Step 3c Convert to rectangular coordinates ($\theta_i+\Delta\theta, \phi_i+\Delta\phi, \rho_i, radius_i$)→($x_i, y_i, z_i, radius_i$)

Step 3d Add random translation ($xn_i, yn_i, zn_i, radius_i$)=($x_i+k_x, y_i+k_y, z_i, radius_i$)

Step 4 Center target coordinates on origin (0,0,0).

Step 4a Find maximum and minimum values of $xn_i$, $yn_i$ and $zn_i$.

Step 4b Find geometric center of receptor $xn_{center}$= ($Xn_{maximum} - xn_{minimum}$)/2 $Yn_{center}$=($yn_{maximum} - Yn_{minimum}$)/2 $zn_{center}$=($zn_{maximum} - zn_{minimum}$)/2

Step 4c Calculate centered coordinates: ($xnc_j, ync_j, znc_j$)= ($xn_i - xn_{center}, yn_i - yn_{center}, zn_j - zn_{maximum}$)

Step 5 Use atomic radii and transformed coordinates ($xnc_i, ync_i, znc_i, radius_i$) to construct collision surface of target $g(x_g, y_g)=z_g$ Step 5a Create a grid with spacing equal to the diameter of the receptor subunits (=1).

Coordinates of grid:

$x_g \in \{Int\ (xn_{minimum} - xn_{center})$, $Int\ (xn_{minimum} - xn_{center})+1 \ldots 0, \ldots Int\ (xn_{maximum} - xn_{center})-1, Int(xn_{maximum} - xn_{center})\}$ $y_g \in \{Int(yn_{minimum} - yn_{center}), Int\ (yn_{minimum}^{-yn}{}_{center})+1 \ldots 0, \ldots Int(_{maximum} - yn_{center})-1, Int\ (yn_{maximum} - yn_{center})\}$ Set the initial values of $g(x_g, y_g)$ to 0 at all points on the grid Step 5b For each atom (i) set the $g(x_g, y_g)$ (height) value of each grid point ($x_g, y_g$) according to the following rule:

For i=1 to number of atoms in target If $(xnc_i - x_p)^2 + (ync_i + y_p)^2 < radius_i^2$ then $g(x_g, y_g)$=minimum ($g(x_g, y_g)$, $znc_i$ $radius_i$)

Else

If $(xnc_i - x_p)^2 + (ync_i + y_p)^2 < (radius_i + 0.5)^2$ then $g(x_g, y_g)$= minimum ($g(x_g, y_g), znc_i - (radius_i/2)$)

Else $g(x_g, y_g)$=minimum ($g(x_g, y_g)$, 0) Next i

Step 6 Center receptor coordinates on origin (0,0).

Step 6a Find maximum and minimum values of $xr_j$, $yr_j$ and $zr_j$.

Step 6b Find geometric center of receptor:

$xr_{center}$=($xr_{maximum} - xr_{minimum}$)/2, $yr_{center}$=($yr_{maximum} - yr_{minimum}$)/2, $zr_{center}$=($zr_{maximum} - zr_{minimum}$)/2

Step 6c Calculate centered receptor coordinates:
$(xc_j, yc_j, zc_j) = (xr_j - x_{center}, yr_j - y_{center}, zr_j - z_{minimum})$.

Step 7 Construct collision surface of receptor $s(x_s, y_s) = z_s$ using the centered receptor coordinates according to the following rule:

Set all initial values of $s(xc_j, yc_j)$ to 0. for j=1 to the number of subunits in receptor if $zc_j > s(xc_j, yc_j)$ then $s(xc_j, yc_j) = zc_j$ next j Step 8 Find minimal separation between collision surface of receptor and collision surface of the target. Calculate difference matrix $d(x_g, y_g)$ as follows for all $x_g \in \{Int(xn_{minimum} - xn_{center}), Int(xn_{minimum} - xn_{center}) + 1 \ldots 0, \ldots Int(xn_{maximum} - xn_{center}) - 1, Int(xn_{maximum} - xn_{center})\}$ and $y_g \in \{Int(yn_{minimum} - y_{center}), Int(yn_{minimum} - yn_{center}) + 1 \ldots 0, \ldots Int(yn_{maximum} - yn_{center}) - 1, Int(yn_{maximum} - yn_{center})\}$ calculate $d(x_g, y_g) = (h(x_g, y_g) - zn_{minimum} + zn_{maximum}) + (s(x_g, y_g) + zr_{minimum} - zr_{maximum})$ For all $x_g, y_g$ find the minimal value of $d(x_g, y_g) = d_{min}$.

$d_{min}$, is the minimal separation distance.

Step 9 Transform target and receptor coordinates for collision configuration

For the receptor:
$(xreceptor_j, yreceptor_j, zreceptor_j) = (xc_j, yc_j, zc_j + zr_{minimum} - zr_{maximum})$ For the target: $(xtarget_i, ytarget_i, ztarget_i) = (xnc_i, ync_i, znc_i - zn_{minimum} + zn_{maximum-dmin})$.

Step 10 Use $(xtarget_i, ytarget_i, ztarget_i)$ and $(xreceptor_j, yreceptor_j, zreceptor_j)$ for affinity calculations.

Repeat Steps 2–9 for each target configuration tested.

Module 5: Affinity Calculation

Step 1 Input collision coordinates of target and receptor $(xtarget_i, ytarget_i, ztarget_i)$ and $(xreceptor_j, yreceptor_j, zreceptor_j)$ where i=number of atoms in target, j=number of subunits in receptor Step 2 Input dipole moment values for target dip(i) Input charge values for receptor charge(j)

Step 3 Input threshold value for proximity calculation: THRESHOLD

Step 4 Calculate dipole affinity value

Step 4a For each charged subunit (charge(j)≠0) calculate $e(i,j) = dip(i)/((xtarget_i - xreceptor_j)^2 + (ytarget_i - yreceptor_j)^2 + (ztarget_i - zreceptor_j)^2)^{1.5}$ Step 4b Calculate the sum of $e(i,j)$ for all combinations of i and j with charge(j)≠0. DIPOLE=$\Sigma \, e(i,j)$ Step 5 Calculate proximity value (this step could be replaced by a calculation based on polarizability)

Step 5a For each target atom with $|dip(j)| \leq 0.75$ Calculate $l(i,j) = ((xtarget_i - xreceptor_j)^2 + (ytarget_i - yreceptor_j)^2 + (ztarget_i - zreceptorc_j)^2)^{0.5}$ If $l(i,j) <$ THRESHOLD then prox(i,j)=1

Step 5b Calculate the sum of prox(i,j) for all combinations of i and j with $|dip(j)| \leq 0.75$ PROXIMITY=$\Sigma$ prox(i,j)

Step 6 Calculate affinity value for target substrate combination=AFFINITY

AFFINITY=(PROXIMITY/j)((PROXIMITY/10000)+DIPOLE)

Module 6: Goodness of Fit Calculation

Step 1 Input known target efficacy or affinity values $(y_k)$, k=number of targets tested Step 2 Input collision coordinates of targets and receptor $(xtarget_i, ytarget_i, ztarget_i)$ and $(xreceptor_j, yreceptor_j, zreceptor_j)$ $i_k$=number of atoms in target k j=number of subunits in receptor Step 3 Input number of target orientations to be tested (=m)

Step 4 Use Module 5 to obtain affinity values for each target and target orientation (=AFFINITY$_{k,m}$).

Step 5 Determine maximum affinity ($MA_k$) and sum affinity ($SA_k$) values for each target.

Step 6 Calculate correlation coefficients $r_{MA}^2$ for maximum affinity ($MA_k$) vs known target efficacy or affinity values ($y_k$) and $r_{SA}^2$ for sum affinity ($SA_k$) vs known target efficacy or affinity values ($y_k$).

Step 7 Calculate fitness coefficient F $F = (r_{MA}^2 \times r_{SA}^2)^{0.5}$

Alternate

Step 6' Calculate correlation coefficients $r_{MA}^2$ for maximum affinity ($MA_k$) vs known target efficacy or affinity values ($y_k$) and $r_{SA-MA}^2$ for sum affinity ($SA_k$)—maximal affinity vs known target efficacy or affinity values ($y_k$)

Step 7' Calculate fitness coefficient F $F = (r_{MA}^2 \times (1 - r_{SA-MA}^2))^{0.5}$

Module 7: Generate Genotype with Minimal Level of Affinity

Step 1 Set minimal fitness threshold

Step 2 Generate random genotype (Module 1)

Step 3 Translate genotype to construct phenotype (Module 2)

Step 4 Test affinity of phenotype for targets (Modules 3, 4, 5, 6)

Step 5 If the fitness of the phenotype exceeds the fitness threshold then discontinue code generation and pass code to phase 2. Otherwise repeat steps 1–5.

Module 8: Multiple Mutation

Step 1 Input primary code (from phase 1).

Step 2 Set number (=q)of mutations per code (Current implementation mutates 2.5–5% of characters in genotype).

Step 3 Input population size (=p).

Step 4 Select a position in the genotype at random.

Step 5 Replace the code character at that position with a different character chosen at random.

Step 6 Repeat steps 4 and 5 until q times. Step 7 Repeat steps 4–6 to generate a total of p new codes.

Step 8 Apply Modules 1–6 to test fitness of mutant population. Select subpopulation with highest selectivity for use in Phase 3.

Module 9: Recombination

Step 1 Set population size (=P).

Step 2 Select two codes at random from population generated by Phase 2.

Step 3 Select a position in the genotype at random.

Step 4 Generate a random number for the number of characters to exchange.

Step 5 Swap characters between codes beginning at selected position.

Step 6 Repeat steps 2–5 until P new genotypes have been generated.

Step 7 Apply Modules 2–6 to test fitness of mutant population. Select subpopulation with highest selectivity for next recombination series or for Phase 4 maturation.

Module 10: Maturation

Step 1 Input parental code derived from Phase 3.

Step 2 Set number of iterations.

Step 3 Select a position in the parental genotype at random.

Step 4 Replace the code character at that position with a different character chosen at random.

Step 5 Test selectivity of parental code ($F_p$) and mutation product ($F_M$) using Modules 2–6.

Step 6 If $F_M \geq F_p$ replace parental genotype with mutation product.

Step 7 Repeat steps 3–6 for required number of iterations.

Module 11: Creation of Code Generating Carbon Skeletons with Rings (6 Member Rings, Entry point=Exit Point)

Step 1. Set length of code

Set v1, v2, v3, . . . vn (frequencies of substituent groups).

Set prob_ring (frequency of ring code sequence). ($0 \leq$ prob_ring $\leq 1$)

Step 2. Initialize prime_code="". Initialize second_code="". Initialize third_code="".

Step 3 Create character strings. Repeat step 4 until code length is obtained.

Step 4a. If prob_ring>random ($0 \leq$ random $\leq 1$) Then Assignment of characters for ring (boat convention).

Set new_character_1 to randomly selected member of {"431413", "314134", "141343", "132132", "321321", "213213", "123123", "231231", "312312", "421412", "214124", "141242", "324234", "242343", "423432"}

Assignment of characters for substituents.

Set new_character_2 to six randomly selected members of {c1, c2, c3, . . . , cn} using frequencies v1, v2, v3, . . . vn. (c1 . . . cn are characters specifying different functional groups)

Assignment of characters for substituent valences.

Set new_character_3 to six randomly selected members of {"1", "2", "3", "4"}

Else

Step 4b. Assignment of single (non-ring) characters for primary code.

Set new_character_1 to a randomly selected member of {"1", "2", "3", "4"}.

Assignment of characters for substituents.

Set new_character_2 to a randomly selected member of {c1, c2, . . . , cn} using frequencies v1, v2, . . . vn.

Assignment of characters for substituent valences.

Set new_character_3 to a randomly selected member of {"1", "2", "3", "4"}.

Step 4c. Concatenate new characters to code strings Prime_code=Prime_code & new_character_1 Second_code=Second_code & new_character_2 Third_code= Third_code & new_character_3

Module 12: Multiple Point Mutation

Step 1 Input primary code.

Step 2 Set number (=q) of mutations per code (Current implementation mutates 2.5–5% of characters in genotype)

Step 3 Input population size (=p).

Step 4 Select a position in the genotype at random.

Step 5 Replace the code characters at that position in each of the code vectors with different characters chosen at random.

Step 6 Repeat steps 4 and 5 until q times.

Step 7 Repeat steps 4–6 to generate a total of p new codes.

Step 8 Test the fitness of each member of the mutant population. Select subpopulation with highest fitness for use in recombination or additional multiple mutation.

Module 13: Sequence Mutations

Step 1 Set $P_{DEL}$, $P_{INV}$, $P_{INS}$, and $P_{DUP}$ as threshold levels for the occurrence of mutations ($0 \leq P_x \leq 1$).

Step 2 Generate a random position (=x) in the code ($0 \leq p \leq$ Length of code).

Step 3 Generate random length of sequence (=L) ($0 \leq L \leq$ Length of code−x).

Step 4 Copy sequence from code starting at x and extending for a total of L characters.

Step 5 If $0 \leq P_{INV} \leq$ Random Number $\leq 1$ Then Reverse the order of the characters in the string.

Step 6 If $0 \leq P_{DUP} \leq$ Random Number $\leq 1$ Then Copy the sequence and concatenate copy to sequence.

Step 7 If $0 \leq P_{DEL} \leq$ Random Number $\leq 1$ Then Eliminate L characters from the code starting at position x Else Replace sequence in code with sequence generated in steps 5 and 6.

Step 8 If $0 \leq P_{INS} \leq$ Random Number $\leq 1$ Then Generate a position (=y) at random in code ($0 \leq y \leq$ Length of code)

Insert sequence generated by steps 5 and 6 at position y.

Module 14: Recombination

Step 1 Set population size (=P)

Step 2 Select two codes at random from population generated by multiple mutation.

Step 3 Select a position in the genotype at random.

Step 4 Generate a random number for the number of characters to exchange.

Step 5 Swap characters between each of the three code vectors beginning at selected position.

Step 6 Repeat steps 2–5 until P new genotypes have been generated.

Step 7 Test the fitness of each ligand in the resulting mutant population. Select subpopulation with highest fitness for next recombination series or for maturation.

Module 15: Maturation

Step 1 Input parental code derived from recombination.

Step 2 Set number of iterations

Step 3 Select a position in the parental genotype at random.

Step 4 Replace the code characters at those positions in each of the code vectors with a different characters chosen at random.

Step 5 Test fitness of parental code ($F_p$) and mutation product ($F_M$) using Modules 4 and 5.

Step 6 If $F_M \geq F_p$ replace parental genotype with mutation product

Step 7 Repeat steps 3–6 for required number of iterations.

What is claimed is:

1. A computer implemented method of designing chemical structures having at least one preselected functional characteristic, comprising the steps of:
   (a) providing a population of receptors having a preselected fitness coefficient for a set of target molecules sharing at least one quantifiable functional characteristic;

(b) providing a simulated model of a chemical structure, calculating an affinity between the chemical structure and each receptor in a plurality of orientations using an affinity calculation, using the calculated affinity to calculate an affinity fitness score;

(c) altering the chemical structure to produce a variant of the chemical structure and repeating step (b); and (d) retaining and further altering those variants of the chemical structure whose affinity score is greater than or equal to a preselected affinity score.

2. The method according to claim 1 wherein said affinity calculation includes at least two measures, the first being a proximity measure wherein the proportion of uncharged portions on said simulated receptors being sufficiently close to non-polar regions on said molecular structure to generate effective London dispersion forces is estimated, and the second being the summed strengths of charge-dipole electrostatic force interactions generated between charged portions of said simulated receptor and dipoles present in said molecular structure.

3. The method according to claim 1 wherein said step of calculating the affinity fitness score includes calculating a sum and maximal affinity between the molecular structure and each receptor, the fitness score being calculated as: $\Sigma\{|\text{calculated maximal affinity} - \text{target maximal affinity}|/\text{target maximal affinity}\}$.

4. The method according to claim 1 wherein said step of calculating the affinity fitness score includes calculating a sum and maximal affinity between the molecular structure and each receptor, the fitness score being calculated as: $\Sigma\{|\text{calculated maximal affinity} - \text{target maximal affinity}|/2\times\text{target maximal affinity})+(|\text{calculated sum affinity} - \text{target sum affinity}|/2\times\text{target sum affinity})\}$.

5. The method according to claim 1 wherein said functional characteristic is biological toxicity.

6. The method according to claim 1 wherein said functional characteristic is catalytic activity.

7. The method according to claim 1 wherein a representation of each computationally designed chemical structure having a preselected affinity score is output.

8. The method according to claim 1 wherein a representation of said variants whose affinity score is greater than or equal to said preselected affinity score is output.

9. The method according to claim 3 or 4 wherein the preselected fitness score is zero.

* * * * *